United States Patent
Tang et al.

(10) Patent No.: US 10,351,580 B2
(45) Date of Patent: Jul. 16, 2019

(54) ACENE-BASED TRANSMITTER MOLECULES FOR PHOTON UPCONVERSION

(71) Applicant: THE REGENTS OF THE UNIVERSITY OF CALIFORNIA, Oakland, CA (US)

(72) Inventors: Ming Lee Tang, Riverside, CA (US); Xin Li, Riverside, CA (US); Zhiyuan Huang, Riverside, CA (US); Melika Mahboub, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/932,326

(22) Filed: Feb. 16, 2018

(65) Prior Publication Data
US 2018/0258111 A1   Sep. 13, 2018

Related U.S. Application Data

(60) Provisional application No. 62/460,555, filed on Feb. 17, 2017.

(51) Int. Cl.
| | | |
|---|---|---|
| *A61B 5/00* | (2006.01) | |
| *A61B 8/00* | (2006.01) | |
| *A61B 10/00* | (2006.01) | |
| *C07F 7/24* | (2006.01) | |
| *A61K 49/00* | (2006.01) | |
| *A61K 9/107* | (2006.01) | |

(52) U.S. Cl.
CPC ............ *C07F 7/24* (2013.01); *A61K 49/0017* (2013.01); *A61K 49/0019* (2013.01); *A61K 49/0021* (2013.01); *A61K 49/0067* (2013.01); *A61K 9/1075* (2013.01)

(58) Field of Classification Search
CPC ... C07F 7/24; A61K 49/0021; A61K 49/0067; A61K 49/0017; A61K 49/0019; A61K 9/1075
USPC ........................................................ 424/9.6
See application file for complete search history.

(56) References Cited

U.S. PATENT DOCUMENTS

| | | | |
|---|---|---|---|
| 9,944,847 B2 | 4/2018 | Baldo et al. | |
| 2011/0013263 A1* | 1/2011 | Miteva | C09K 11/06 359/326 |
| 2012/0161076 A1* | 6/2012 | Kahn | B82Y 30/00 252/301.16 |
| 2012/0217477 A1* | 8/2012 | So | B82Y 30/00 257/21 |

OTHER PUBLICATIONS

Huang et al. Nano Lett. 2015, 15, 5552-5557.*
Dorfs et al. J. Am. Chem. Soc. 2011, 133, 11175-11180.*
Kanehara et al. J. Am. Chem. Soc. 2009, 131, 17736-17737.*
Jintoku et al. J. Mat. Chem. C, 2015, 3, 5970.*
Gianella et al. ACSNANO 2011, 6, 4422-4433.*
Wang et al. Biomat. 2011, 32, 1110-1120.*
He et al. NanoLett. 2008, 8, 2688-2692.*
Carbone, et al., Synthesis and Micrometer-Scale Assembly of Colloidal CdSe/CdS Nanorods Prepared by a Seeded Growth Approach, Nano Letters, 2007, pp. 2942-2950, vol. 7, No. 10.
Hines, et al., Colloidal PbS Nanocrystals with Size-Tunable Near-Infrared Emission: Observation of Post-Synthesis Self-Narrowing of the Particle Size Distribution, Advanced Materials, Nov. 4 2003, pp. 1844-1849, vol. 15, No. 21.
Huang, et al., Hybrid Molecule-Nanocrystal Photon Upconversion Across the Visible and Near-Infrared, Nano Letters, 2015, pp. 5552-5557, vol. 15.
Huang, et al., Ligand Enhanced Upconversion of Near-Infrared Photons with Nanocrystal Light Absorbers, The Royal Society of Chemistry, 2016, pp. 4101-4104, vol. 7.
Ma, et al., Photovoltaic Performance of Ultra-Small PbSe Quantum Dots, Lawrence Berkeley National Laboratory, Apr. 21, 2014, 24 pages.
Monguzzi, et al., Upconversion-induced Fluorescence in Multicomponent Systems: Steady-State Excitation Power Threshold, Physical Review B, 2008, pp. 195112-1-195112-5, vol. 78.
Ogawa, et al., Highly Efficient Photon Upconversion in Self-Assemble Light-Harvesting Molecular Systems, Scientific Reports, Jun. 9, 2015, 9 pages.
Yu, et al., Experimental Determination of the Extinction Coefficient of CdTe, CdSe, and CdS Nanocrystals, Chem. Mater., Jun. 7, 2003, pp. 2854-2860, vol. 15.

* cited by examiner

*Primary Examiner* — Michael G. Hartley
*Assistant Examiner* — Sean R Donohue
(74) *Attorney, Agent, or Firm* — Mintz, Levin, Cohn, Ferris, Glovsky and Popeo, P.C.

(57) ABSTRACT

Provided herein are transmitter ligands that improve photon upconversion of near infrared light (NIR) to visible light. The presently provided ligands are complexed to semiconductor nanocrystals and improve triplet energy transfer from semiconductor nanocrystal to annihilator in triplet-triplet annihilation. Suitable applications include bio-imaging.

16 Claims, 10 Drawing Sheets

ACENE-BASED TRANSMITTER MOLECULES FOR PHOTON UPCONVERSION

CROSS-REFERENCES TO RELATED APPLICATIONS

This application claims the benefit of priority under 35 U.S.C. § 119(e) to U.S. Provisional Application Ser. No. 62/460,555 filed Feb. 17, 2017, the disclosure of which is incorporated herein by reference in its entirety.

STATEMENT AS TO RIGHTS TO INVENTIONS MADE UNDER FEDERALLY SPONSORED RESEARCH AND DEVELOPMENT

This invention was made with Government support under Grant No. W911NF-15-1-0-040, awarded by the ARMY/ARO and the National Science Foundation under Grant No. CHE1351663. The Government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Photon upconversion is a promising wavelength-shifting technology for photon management. This multi-photon process has potential applications in biological imaging, photocatalysis and photovoltaics.

Multi-excitonic processes can be harnessed to reorganize the energy contained in photons in order to improve the performance of photovoltaic devices or photocatalysts. Reshaping the solar spectrum to match the optical properties of common semiconductors will allow the efficient use of all incident light. While many efforts e.g. hot carrier devices, intermediate band or multi-exciton generation solar cells, offer a route to manipulating incoming photons, the conversion of low energy near-infrared (NIR) photons to higher energy photons is particularly appealing, especially when considering NIR radiation comprises 53% of the solar spectrum.

The upconversion of NIR photons at the solar flux has not been demonstrated. If this formidable challenge is met, sub-bandgap photons that are currently not absorbed by common semiconductors can be utilized. Photon upconversion is predicted to increase the power conversion efficiency of a single p-n junction silicon solar cell from 28% to 43%, beyond the Shockley-Queisser limit. Currently, the upconversion of incident photons at power densities commensurate with the solar flux has only been demonstrated for the conversion of green to violet light, via a triplet-triplet annihilation (TTA) based mechanism. This is because other upconverting platforms, like the lanthanides or the chromophores for multi-photon absorption (used in bioimaging) require high excitation densities for appreciable efficiency. TTA-based photon upconversion can be efficient when molecular or nanocrystal (NC) light absorbers are used to sensitize triplet states on molecules. Two triplets can encounter each other and undergo TTA to emit a high-energy photon. Internal upconversion quantum yields (QYs) as high as 35% and 14% have been reported for the upconversion of green to violet light with palladium porphyrins and CdSe NCs as sensitizers respectively. However, in terms of harvesting NIR photons, molecular sensitizers that absorb strongly in the NIR generally have low fluorescence QYs due to strong internal conversion, as predicted by the energy gap law. In contrast, the size, shape and material dependent optical properties of NCs make them ideal as light absorbers for photon upconversion.

From the foregoing, it can be seen that there is a need in the art to prepare nanocrystal transmitter ligands that can provide general, reliable, and efficient upconversion of low energy near-infrared incident photons to higher energy photons. The present disclosure provides this and other advantages as well.

BRIEF SUMMARY OF THE INVENTION

In one aspect, provided herein are nanocrystal transmitter ligand complexes for photon upconversion comprising a semi-conductor nanocrystal and a transmitter ligand of Formula I, II, III, or a combination thereof

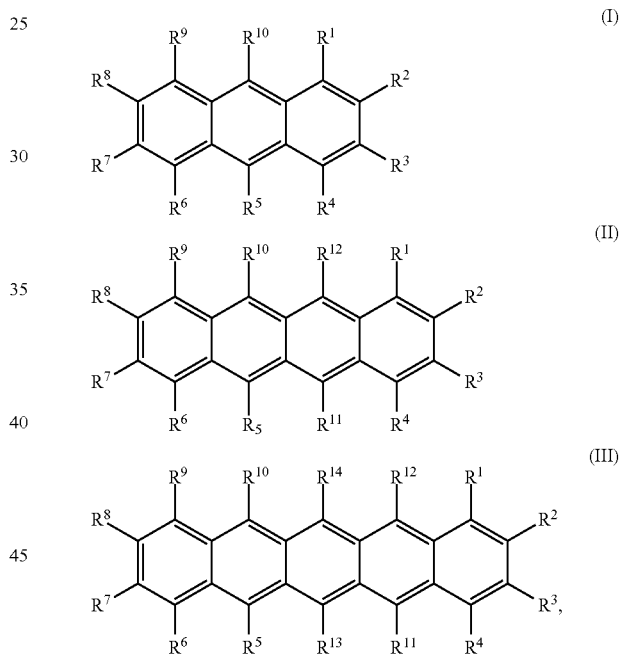

wherein $R^1$ to $R^{14}$ are as defined below.

In some aspect, provided herein are photon upconversion hybrid systems comprising a nanocrystal transmitter ligand complex and an annihilator.

In some aspects, provided herein are transmitter ligands of Formula I, II, or III

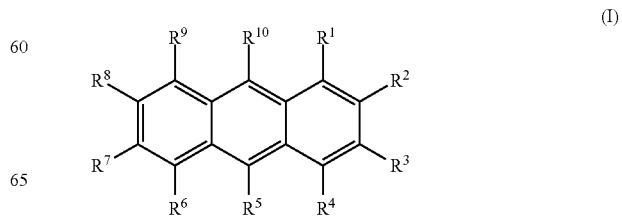

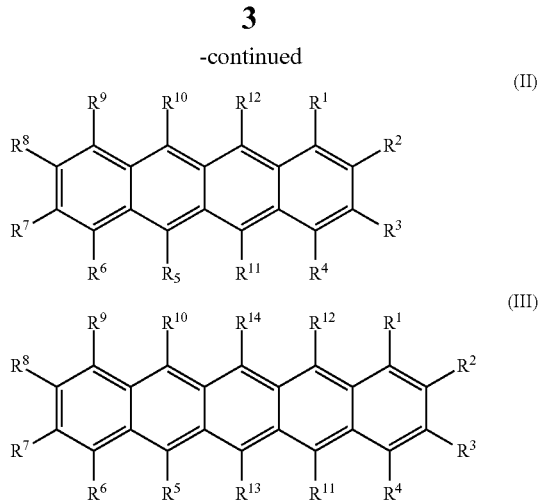

(II)

(III)

wherein $R^1$ to $R^{14}$ are as defined below.

In some aspect, provided herein are methods of non-invasive bio-imaging and/or non-invasive bio-detection, said method comprising administering to a subject one or more nanocrystal transmitter ligand complexes described herein.

DETAILED DESCRIPTION OF THE INVENTION

I. General

Figure 1:
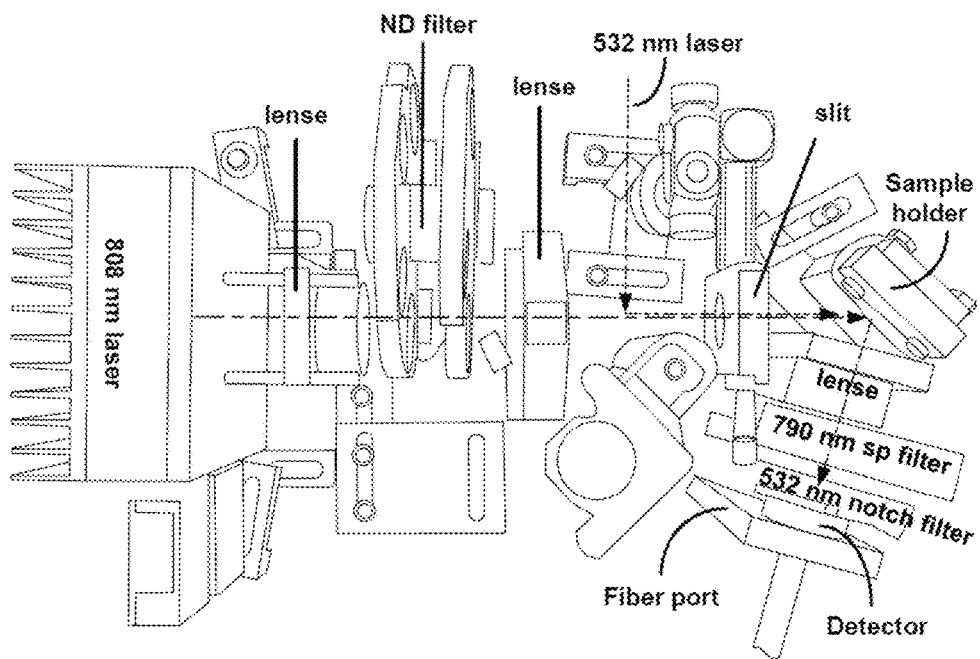
FIG. 1 shows the upconversion measurement set up. Further details of the set up are provided in the Examples.

Provided herein are transmitter ligands of Formula I, II, and III that vastly increase the upconversion QY of photons in nanocrystal transmitter ligand complex and photon upconversion hybrid systems. Previous nanoparticle-ligand complexes suffered from inefficiencies such as low quantum yield and require high powered lasers. The current disclosure addresses the deficiencies in the art and provide improved means for applications such as bio-imaging.

In particular, the advantageous photon upconversion properties of the nanocrystal transmitter ligand complexes of the present disclosure make these complexes ideal for non-invasive bio-imaging. The nanocrystal-transmitter complexes described herein provide a means for delivering optical triggers into tissue and organs in the near infrared (NIR) windows I and II. Further, the nanocrystal transmitter ligand complexes of the present disclosure minimize photodamage and background scattering, with the advantages of multi-photon absorption microscopy at a fraction of the cost by eliminating expensive femtosecond pulsed lasers and laser scanners. The low excitation power densities and simultaneous recording of all fluorophores within the field of view addresses current bottlenecks for long-duration imaging of thick tissues, e.g. organs like the brain. In terms of photoacoustic imaging, this nanomaterial platform can be designed to form the ideal contrast agent that absorbs strongly in the NIR and dissipates acoustic waves. This decreases reliance on endogenous markers and advances the imaging of microvasculature by increasing the penetration depth and enabling spectroscopic quantification. The efficient production of UV and visible light from NIR light facilitates the development of safer fiducial markers for cancers such as breast cancer compared to the current radioactive tracers.

II. Definitions

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene. Alkenylen groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkynylene" refers to an alkynyl group, as defined above, linking at least two other groups, i.e., a divalent hydrocarbon radical. The two moieties linked to the alkynylene can be linked to the same-atom or different atoms of the alkynylene. Alkynylene groups include, but are not limited to, ethynylene, propynylene, isopropynylene, butynylene, sec-butynylene, pentynylene and hexynylene. Alkynylene groups can be substituted or unsubstituted.

"Phenylene" refers to a phenyl group linking at least two other groups, i.e., a divalent phenyl radical. In some embodiments, phenylene refers to the following structure

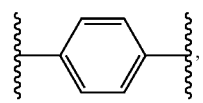 [SMILES: *c1ccc(*)cc1]

where the wavy lines indicate points of attachment to other groups

"Bi-phenylene" refers to a bi-phenyl group linking at least two other groups, i.e., a divalent bi-phenyl radical. In some embodiments, bi-phenylene refers to the following structure

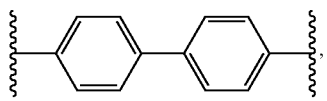

where the wavy lines indicate points of attachment to other groups.

The term "silyl" as used herein includes —SiR$^b$R$^c$R$^d$ K groups wherein R$^b$, R$^c$, and R$^d$ are C$_{1-30}$ alkyl or aryl. In some embodiments, R$^b$, R$^c$, and R$^d$ are C$_{1-10}$ alkyl or aryl. Particular "silyl" groups include, but are not limited to trimethylsilyl, triethylsilyl, and tertbutyldimethylsilyl, tert-Butyldiphenylsilyl, and Triisopropylsilyl. The term "silyloxy" refers to silyl ethers of formula —O—SiR$^d$R$^e$R$^f$.

The term "upconversion", or in short "UC", used herein refers to a process in which the sequential absorption of two or more photons leads to the emission of light at shorter wavelength than the excitation wavelength.

The term "nanoparticle" used herein refers to a particle which has an average size of 100 nm to 1 nm, or otherwise specified in the present application.

III. Detailed Description of Embodiments

A. Nanocrystal Transmitter Ligand Complexes for Photon Upconversion

In one aspect, provided herein are nanocrystal transmitter ligand complexes for photon upconversion comprising a semi-conductor nanocrystal and a transmitter ligand of Formula I, II, III, or a combination thereof

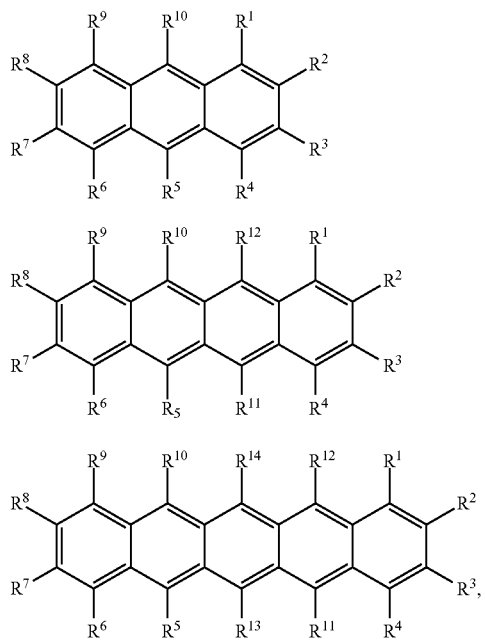

wherein,
R$^1$, R$^2$, R$^3$, R$^4$, R$^5$, R$^6$, R$^7$, R$^8$, R$^9$, R$^{10}$, R$^{11}$, R$^{12}$, R$^{13}$, and R$^{14}$ are independently selected from the group consisting of H, —X$^1$—C(O)OH, —X$^1$—C(S)SH, —X$^1$—C(O)SH, —X$^1$—C(S)OH, —X$^1$—NH—C(O)OH, —X$^1$—NH—C(S)SH, —X$^1$—NH—C(O)SH, —X$^1$—NH—C(S)OH, —X$^1$—P(O)(OH)$_2$, —X$^1$—OP(O)(OH)$_2$, silyl, silyloxy, and a 6-membered heteroaryl comprising at least one nitrogen atom;
wherein at least 1 but not more than 4 of R$^1$ to R$^{14}$ are not H;
X$^1$ is selected from the group consisting of a bond, phenylene, bi-phenylene, C$_1$-C$_{10}$ alkylene, C$_1$-C$_{10}$ alkenylene, C$_1$-C$_{10}$ alkynylene, C$_1$-C$_{10}$ alkylenephenylene, phenylene-C$_1$-C$_{10}$ alkylene, C$_1$-C$_{10}$ alkenylene phenylene, phenylene-C$_1$-C$_{10}$ alkenylene, C$_1$-C$_{10}$ alkynylene phenylene, phenylene-C$_1$-C$_{10}$ alkynylene, C$_1$-C$_{10}$ alkylenebi-phenylene, bi-phenylene-C$_1$-C$_{10}$ alkylene, C$_1$-C$_{10}$ alkenylenebi-phenylene, bi-phenylene-C$_1$-C$_{10}$ alkenylene, C$_1$-C$_{10}$ alkynylene bi-phenylene, bi-phenylene-C$_1$-C$_{10}$ alkynylene, phenylene-O—C$_1$-C$_{10}$ alkylene, phenylene-O—C$_1$-C$_{10}$ alkenylene, phenylene-O—C$_1$-C$_{10}$ alkynylene, phenylene-S—C$_1$-C$_{10}$ alkylene, phenylene-S—C$_1$-C$_{10}$ alkenylene, and phenylene-S—C$_1$-C$_{10}$ alkynylene,
provided that said compound is not
4-((13-((triisopropylsilyl)ethynyl)pentacen-6-yl)ethynyl)benzoic acid.

In some embodiments, the semiconductor nanocrystal is selected from the group consisting of a copper semiconductor nanocrystal, a cadmium semiconductor nanocrystal, an indium semiconductor nanocrystal, a lead semiconductor nanocrystal, a tin semiconductor nanocrystal, an aluminum semiconductor nanocrystal, and a silicon semiconductor nanocrystal.

In some embodiments, the copper semiconductor nanocrystal is selected from the group consisting of CuS, CuSe, CuTe.

In some embodiments, the cadmium semiconductor nanocrystal is selected from the group consisting of CdS, CdSe, CdTe.

In some embodiments, the lead semiconductor nanocrystal is selected from the group consisting of PbS, PbSe, PbTe.

In some embodiments, the indium semiconductor nanocrystal is indium tin oxide.

In some embodiments, the aluminum semiconductor nanocrystal is aluminum tin oxide.

In some embodiments, the transmitter ligand is represented by a compound of Formula I

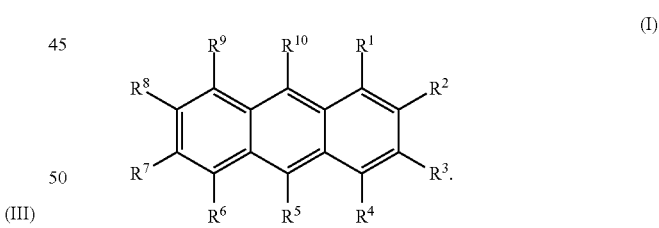

In some embodiments, the transmitter ligand is represented by a compound of Formula II

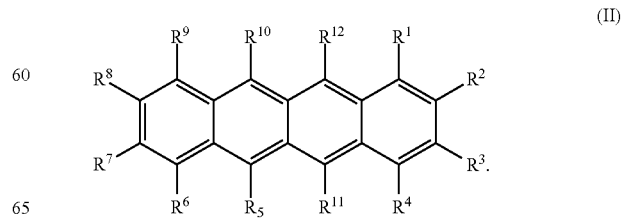

In some embodiments, the transmitter ligand is represented by a compound of Formula III

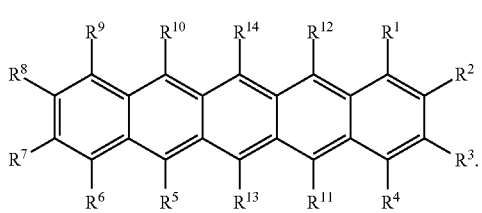
(III)

In some embodiments, one of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is other than H.

In some embodiments, two of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is other than H.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of H, —$X^1$—C(O)OH, —$X^1$—C(S)SH, —$X^1$—C(O)SH, —$X^1$—C(S)OH, —$X^1$—NH—C(O)OH, —$X^1$—NH—C(S)SH, —$X^1$—NH—C(O)SH, and —$X^1$—NH—C(S)OH.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of H, —$X^1$—C(O)OH, —$X^1$—C(S)SH, —$X^1$—NH—C(O)OH, and —$X^1$—NH—C(S)SH.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of H, —$X^1$—C(O)OH, —$X^1$—C(S)SH, and —$X^1$—NH—C(S)SH.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of H, —$X^1$—C(O)OH, and —$X^1$—C(S)SH.

In some embodiments, the 6-membered heteroaryl comprising at least one nitrogen atom is selected from the group consisting of pyridine and pyrimidine In some embodiments, each $X^1$ is selected from the group consisting of a bond, phenylene, bi-phenylene.

In some embodiments, each $X^1$ is selected from the group consisting of $C_{1-10}$ alkylene, $C_{1-10}$ alkenylene, and $C_{1-10}$ alkynylene.

In some embodiments, each $X^1$ is selected from the group consisting of $C_{1-10}$ alkylene-phenylene, phenylene-$C_{1-10}$ alkylene, $C_{1-10}$ alkenylene-phenylene, phenylene-$C_{1-10}$ alkenylene, $C_{1-10}$ alkynylene-phenylene, phenylene-$C_{1-10}$ alkynylene, $C_{1-10}$ alkylene-bi-phenylene, bi-phenylene-$C_{1-10}$ alkylene, $C_{1-10}$ alkenylene-bi-phenylene, bi-phenylene-$C_{1-10}$ alkenylene, $C_{1-10}$ alkynylene-bi-phenylene, and bi-phenylene-$C_{1-10}$ alkynylene.

In some embodiments, each $X^1$ is selected from the group consisting of phenylene-O—$C_1$-$C_{10}$ alkylene, phenylene-O—$C_1$-$C_{10}$ alkenylene, phenylene-O—$C_1$-$C_{10}$ alkynylene, phenylene-S—$C_1$-$C_{10}$ alkylene, phenylene-S—$C_1$-$C_{10}$ alkenylene, and phenylene-S—$C_1$-$C_{10}$ alkynylene.

In some embodiments, the transmitter ligand is represented by Formula Ia, Ib, or Ic

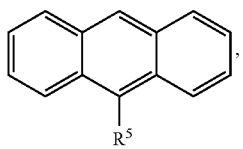
(Ia)

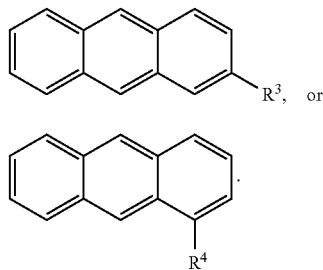
(Ib)

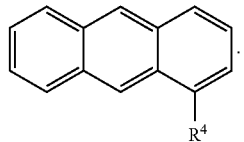
(Ic)

In some embodiments, the transmitter ligand is represented by Formula IIa, IIb, or IIc

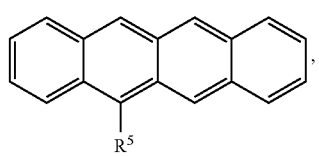
(IIa)

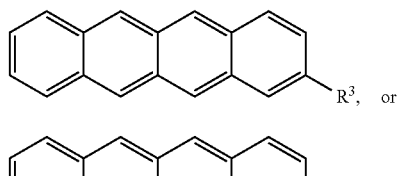
(IIb)

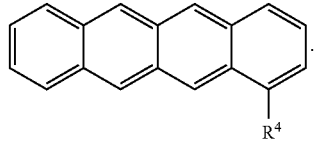
(IIc)

In some embodiments, the transmitter ligand is represented by Formula IIIa, IIIb, IIIc, or IIId

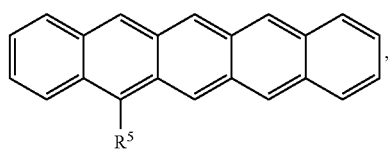
(IIIa)

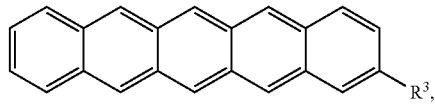
(IIIb)

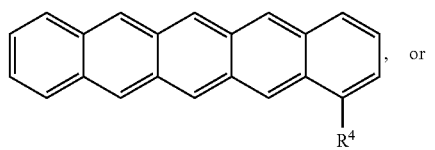
(IIIc)

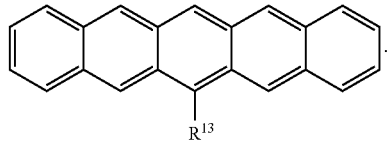
(IIId)

In some embodiments, the transmitter ligand is a compound discussed in section C, below.

Methods of making the nanocrystals described herein are known in the art. The nanocrystal transmitter ligand complexes of the current disclosure can be made, for example, via ligand exchange as detailed in Example 3 of the present disclosure.

B. Photon Upconversion Hybrid Systems

In some aspects, provided herein are photon upconversion hybrid systems comprising a nanocrystal transmitter ligand complex described supra and an annihilator.

In the photon upconversion hybrid system the nanocrystal absorbs low energy photons that are then transferred as triples to the transmitter ligand bound to the nanocrystal surface. Triplet energy transfer (TET) then occurs again down an energy cascade, from the transmitter ligand to the annihilator. Two annihilator molecules in their triplet-excited state collide in a spin-allowed energy conserved manner known as triplet-triplet annihilation to emit a higher energy photon.

Suitable annihilators include those with conjugated pi systems that can accept the triplet energy transfer from the transmitter ligands of the present disclosure. Such annihilators include, but are not limited to 9,10-diphenylanthracene (DPA), 9-(4-phenylethynyl)-10-phenylanthracene, 9,10-bis(phenylethynyl)anthracene (BPEA), pyrene, BODIPY dye molecules, and rubrene.

C. Transmitter Ligands

In another aspect, provided herein are transmitter ligands of Formula I, II, or III

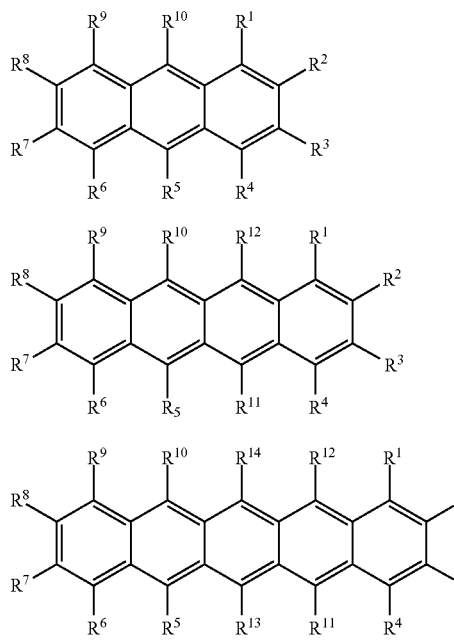

wherein,
$R^1, R^2, R^3, R^4, R^5, R^6, R^7, R^8, R^9, R^{10}, R^{11}, R^{12}, R^{13}$, and $R^{14}$ are independently selected from the group consisting of H, —$X^1$—C(O)OH, —$X^1$—C(S)SH, —$X^1$—C(O)SH, —$X^1$—C(S)OH, —$X^1$—NH—C(O)OH, —$X^1$—NH—C(S)SH, —$X^1$—NH—C(O)SH, —$X^1$—NH—C(S)OH, —$X^1$—P(O)(OH)$_2$, —$X^1$—O—P(O)(OH)$_2$, silyl, silyloxy, and a 6-membered heteroaryl comprising at least one nitrogen atom;
wherein at least 1 but not more than 4 of $R^1$ to $R^{14}$ are not H;

$X^1$ is selected from the group consisting of a bond, phenylene, bi-phenylene, $C_1$-$C_{10}$ alkylene, $C_1$-$C_{10}$ alkenylene, $C_1$-$C_{10}$ alkynylene, $C_1$-$C_{10}$ alkylenephenylene, phenylene-$C_1$-$C_{10}$ alkylene, $C_1$-$C_{10}$ alkenylene phenylene, phenylene-$C_1$-$C_{10}$ alkenylene, $C_1$-$C_{10}$ alkynylene phenylene, phenylene-$C_1$-$C_{10}$ alkynylene, $C_1$-$C_{10}$ alkylenebi-phenylene, bi-phenylene-$C_1$-$C_{10}$ alkylene, $C_1$-$C_{10}$ alkenylenebi-phenylene, bi-phenylene-$C_{1-10}$ alkenylene, $C_{1-10}$ alkynylene bi-phenylene, bi-phenylene-$C_{1-10}$ alkynylene, phenylene-O—$C_1$-$C_{10}$ alkylene, phenylene-O—$C_1$-$C_{10}$ alkenylene, phenylene-O—$C_1$-$C_{10}$ alkynylene, phenylene-S—$C_1$-$C_{10}$ alkylene, phenylene-S—$C_1$-$C_{10}$ alkenylene, and phenylene-S—$C_1$-$C_{10}$ alkynylene,
wherein at least 1 $X^1$ is other than a bond.

In some embodiments, the transmitter ligand is represented by a compound of Formula I

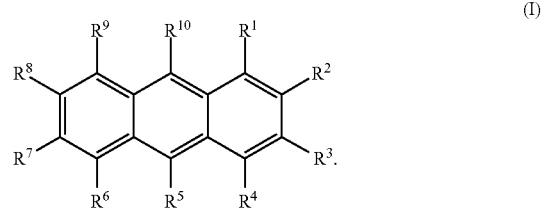

In some embodiments, the transmitter ligand is represented by a compound of Formula II

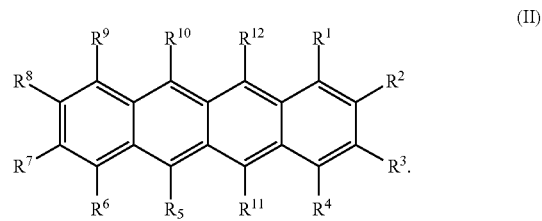

In some embodiments, the transmitter ligand is represented by a compound of Formula III

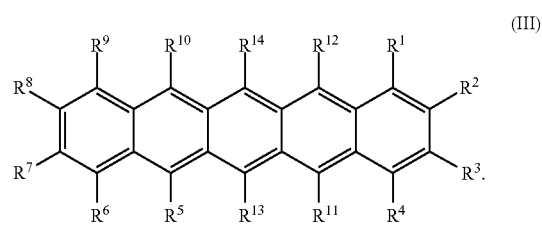

In some embodiments, one of $R^1, R^2, R^3, R^4, R^5, R^6, R^7, R^8, R^9, R^{10}, R^{11}, R^{12}, R^{13}$, and $R^{14}$ is other than H.

In some embodiments, two of $R^1, R^2, R^3, R^4, R^5, R^6, R^7, R^8, R^9, R^{10}, R^{11}, R^{12}, R^{13}$, and $R^{14}$ is other than H.

In some embodiments, $R^1, R^2, R^3, R^4, R^5, R^6, R^7, R^8, R^9, R^{10}, R^{11}, R^{12}, R^{13}$, and $R^{14}$ are independently selected from the group consisting of H, —$X^1$—C(O)OH, —$X^1$—C(S)SH, —$X^1$—C(O)SH, —$X^1$—C(S)OH, —$X^1$—NH—C(O)OH, —$X^1$—NH—C(S)SH, —$X^1$—NH—C(O)SH, and —$X^1$—NH—C(S)OH.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of H, —$X^1$—C(O)OH, —$X^1$—C(S)SH, —$X^1$—NH—C(O)OH, and —$X^1$—NH—C(S)SH.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of H, —$X^1$—C(O)OH, —$X^1$—C(S)SH, and —$X^1$—NH—C(S)SH.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are independently selected from the group consisting of H, —$X^1$—C(O)OH, and —$X^1$—C(S)SH.

In some embodiments, the 6-membered heteroaryl comprising at least one nitrogen atom is selected from the group consisting of pyridine and pyrimidine In some embodiments, each $X^1$ is selected from the group consisting of a bond, phenylene, bi-phenylene.

In some embodiments each $X^1$ is selected from the group consisting of $C_{1-10}$ alkylene, $C_{1-10}$ alkenylene, and $C_{1-10}$ alkynylene.

In some embodiments, each $X^1$ is selected from the group consisting of $C_{1-10}$ alkylene phenylene, phenylene-$C_{1-10}$ alkylene, $C_{1-10}$ alkenylene phenylene, phenylene-$C_{1-10}$ alkenylene, $C_{1-10}$ alkynylene phenylene, phenylene-$C_{1-10}$ alkynylene, $C_{1-10}$ alkylenebi-phenylene, bi-phenylene-$C_{1-10}$ alkylene, $C_{1-10}$ alkenylene bi-phenylene, bi-phenylene-$C_{1-10}$ alkenylene, $C_{1-10}$ alkynylene-bi-phenylene, and bi-phenylene-$C_{1-10}$ alkynylene.

In some embodiments, each $X^1$ is selected from the group consisting of phenylene-O—$C_1$-$C_{10}$ alkylene, phenylene-O—$C_1$-$C_{10}$ alkenylene, phenylene-O—$C_1$-$C_{10}$ alkynylene, phenylene-S—$C_1$-$C_{10}$ alkylene, phenylene-S—$C_1$-$C_{10}$ alkenylene, and phenylene-S—$C_1$-$C_{10}$ alkynylene.

In some embodiments, the transmitter ligand is represented by Formula Ia, Ib, or Ic

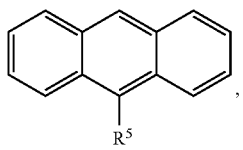
(Ia)

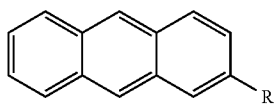
(Ib)

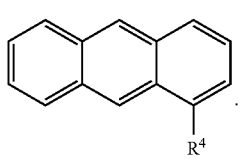
(Ic)

In some embodiments, the transmitter ligand is represented by Formula IIa, IIb, or IIc

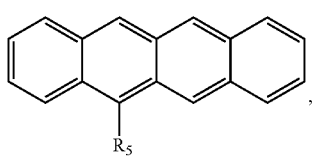
(IIa)

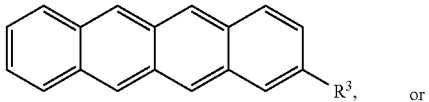
(IIb)

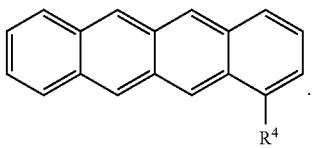
(IIc)

In some embodiments, the transmitter ligand is represented by Formula IIIa, IIIb, IIIc, or IIId

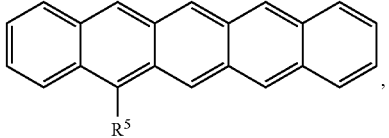
(IIIa)

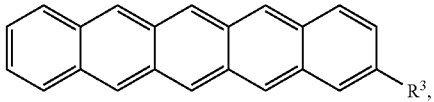
(IIIb)

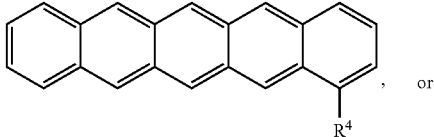
(IIIc)

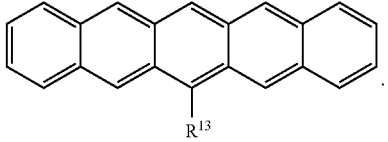
(IIId)

In some embodiments the transmitter ligand has the formula selected from the group consisting of

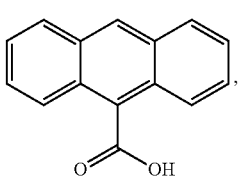 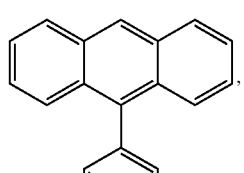

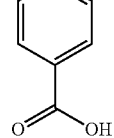

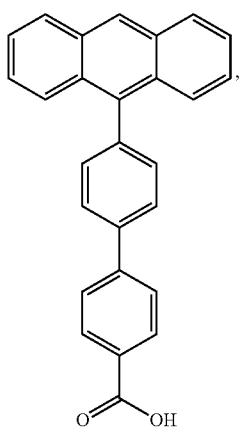
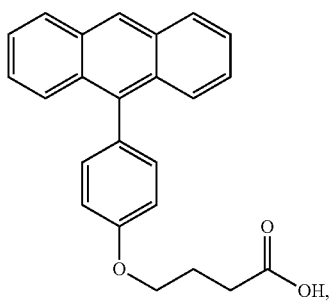
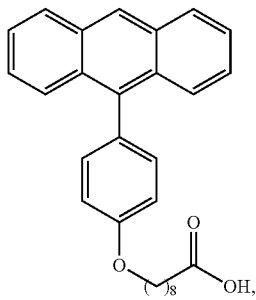
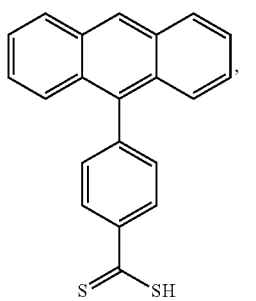
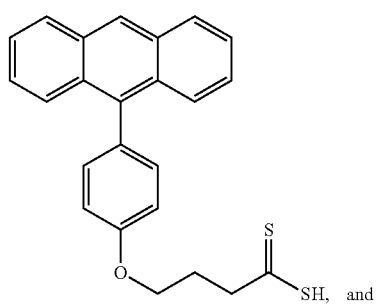
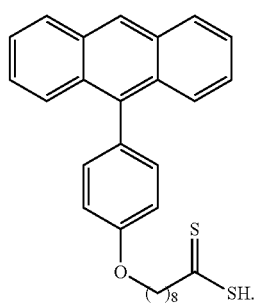
In some embodiments the transmitter ligand has the formula selected from the group consisting of
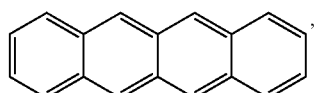
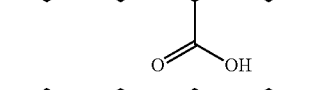
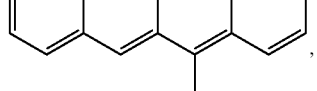
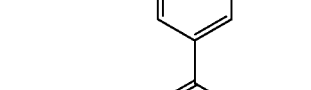
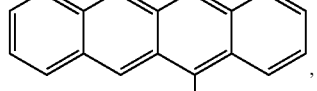
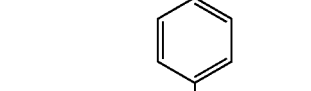
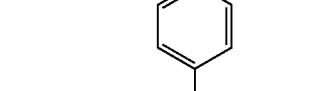

-continued
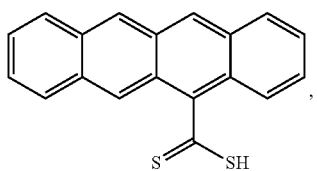,
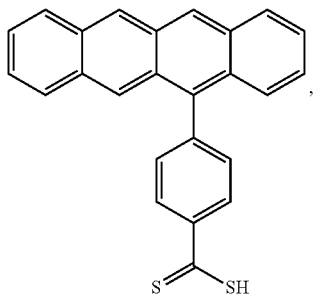, and
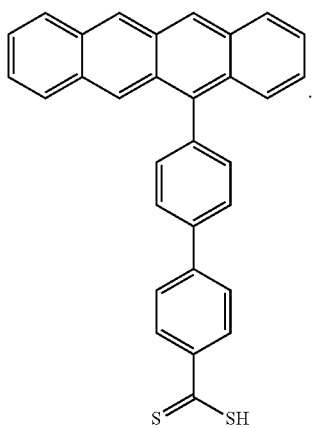.
In some embodiments the transmitter ligand has the formula selected from the group consisting of
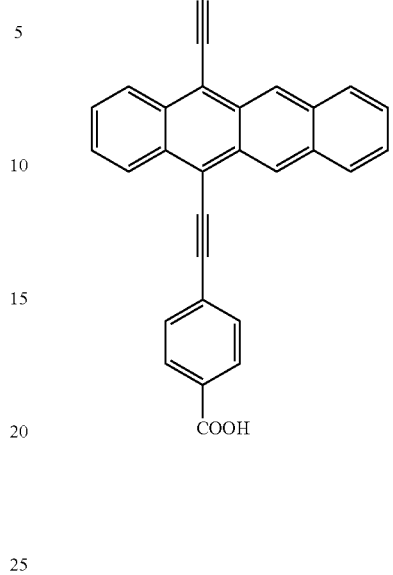
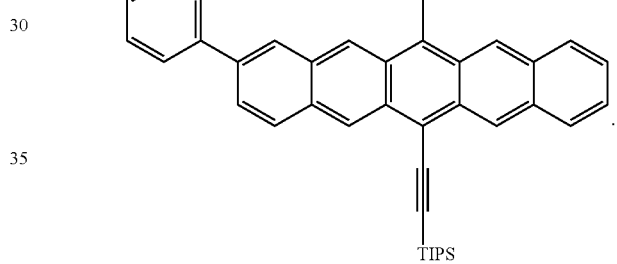.
In some embodiments the transmitter ligand has the formula selected from the group consisting of
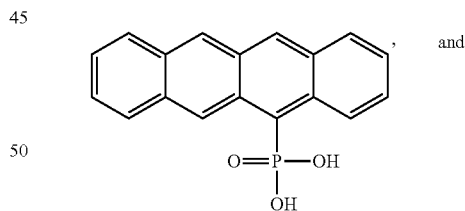, and
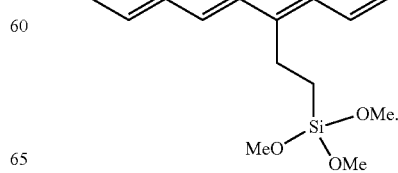

In some embodiments the transmitter ligand has the formula selected from the group consisting of

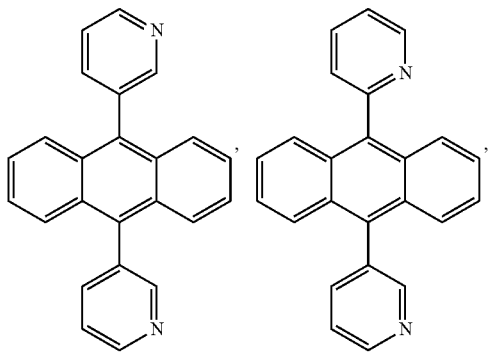, and 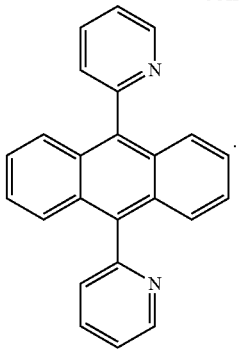

Methods of making the transmitter ligands of Formula I, II, or III are further described in the Examples of this application. In general, standard synthesis steps such as Suzuki coupling, transesterification, and oxidation are used from known starting materials such as 4-bromophenol and anthracene.

As a non-limiting example, particular transmitter molecules can be synthesized using Scheme A, below.

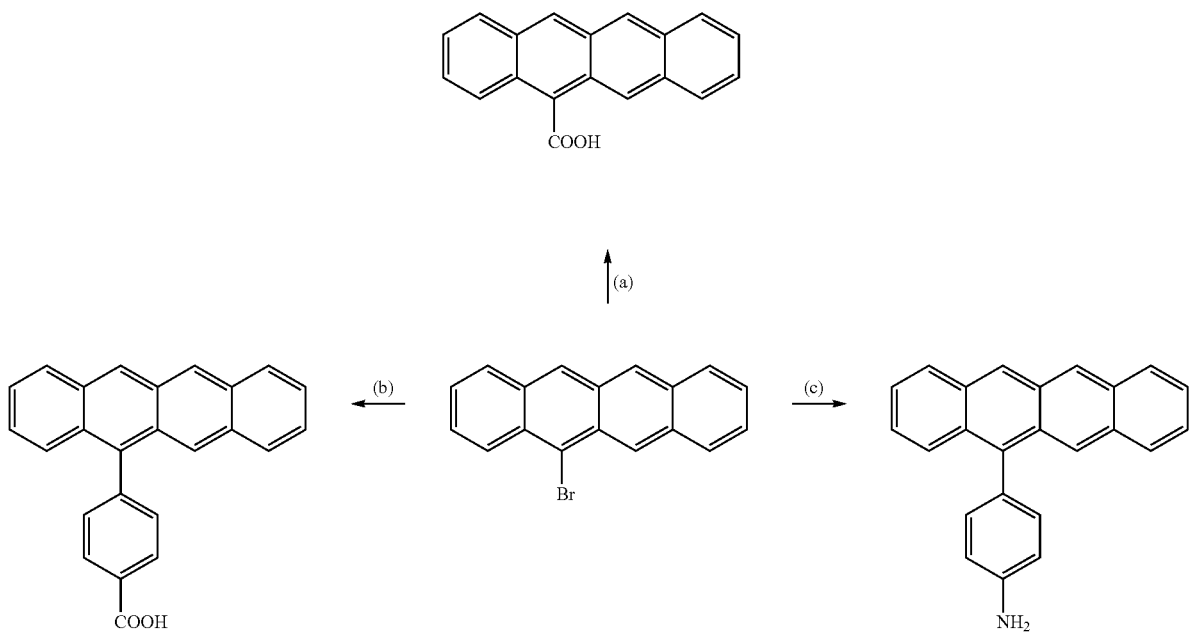

Scheme A: a) nBuLi, then $CO_{2\,(g)}$, THF, 70% following Chem. Asian J. 2012, 7, 105; b) (i) 4-(ethoxylcarbonyl)phenylboronic acid, $Cs_2CO_3$, $PhCH_3$, $Pd(dppf)Cl_2$, 60° C., then (ii) $KOH_{(aq)}$, THF, MeOH, reflux, 90% overall; c) 4-aminophenylboronic acid, $K_2CO_3$, $PhCH_3$, EtOH, $H_2O$, $Pd(PPh_3)_4$, 80° C., 90%.

As additional non-limiting examples, particular transmitter molecules can be synthesized using Scheme B, Scheme C, or Scheme D, below.

Scheme B
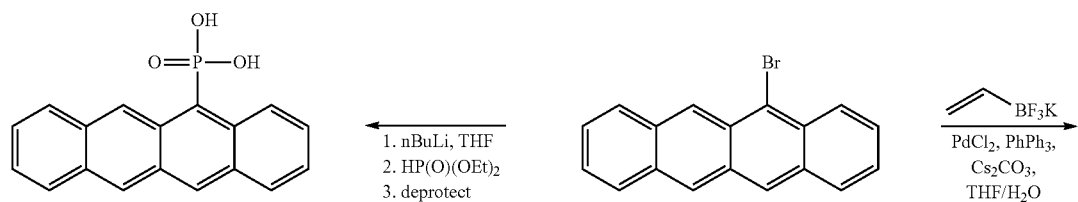
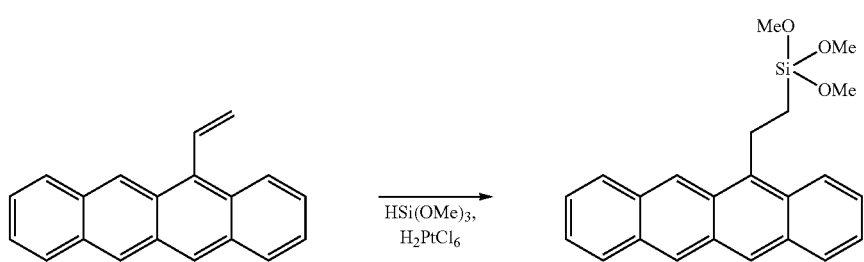
Scheme C
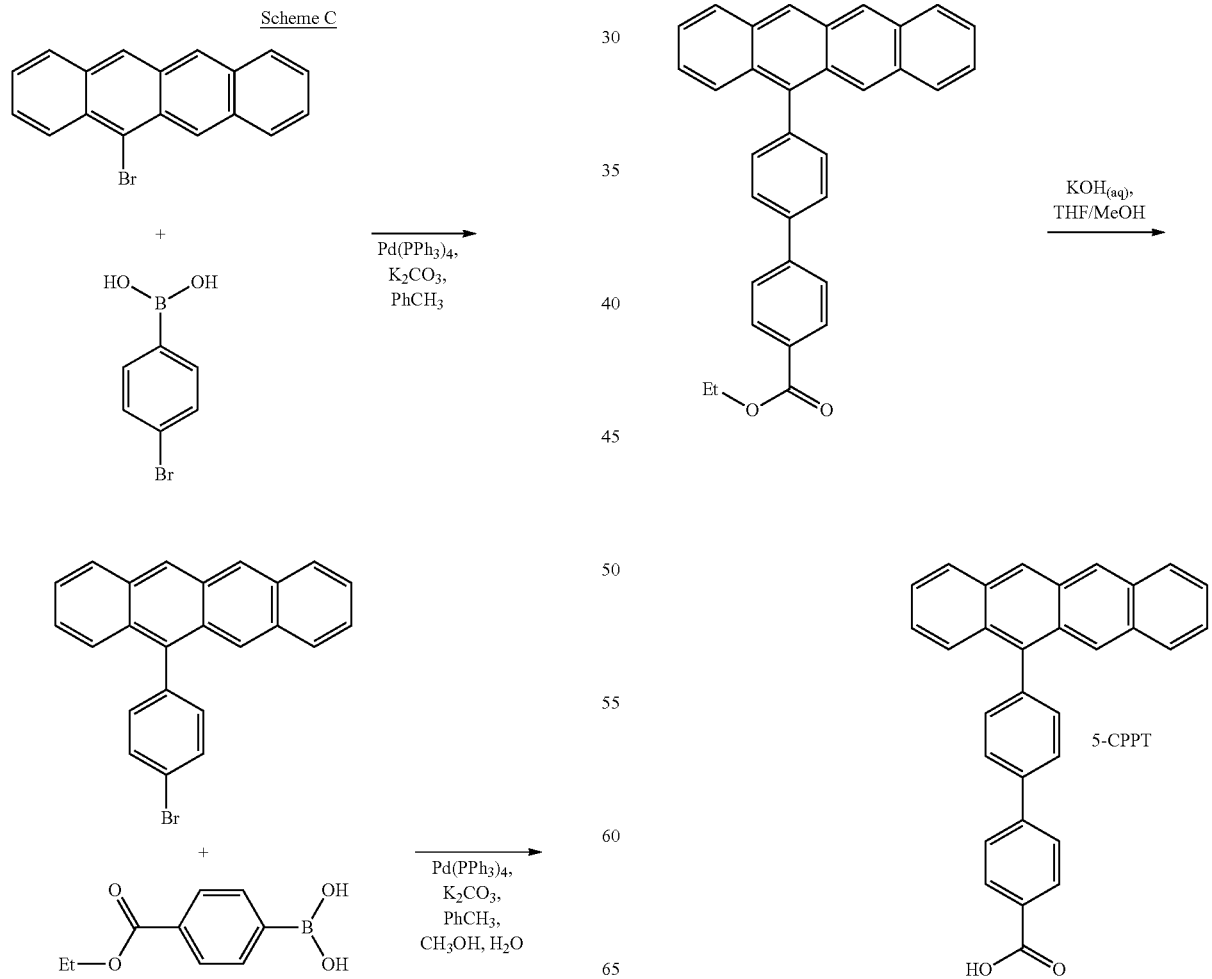

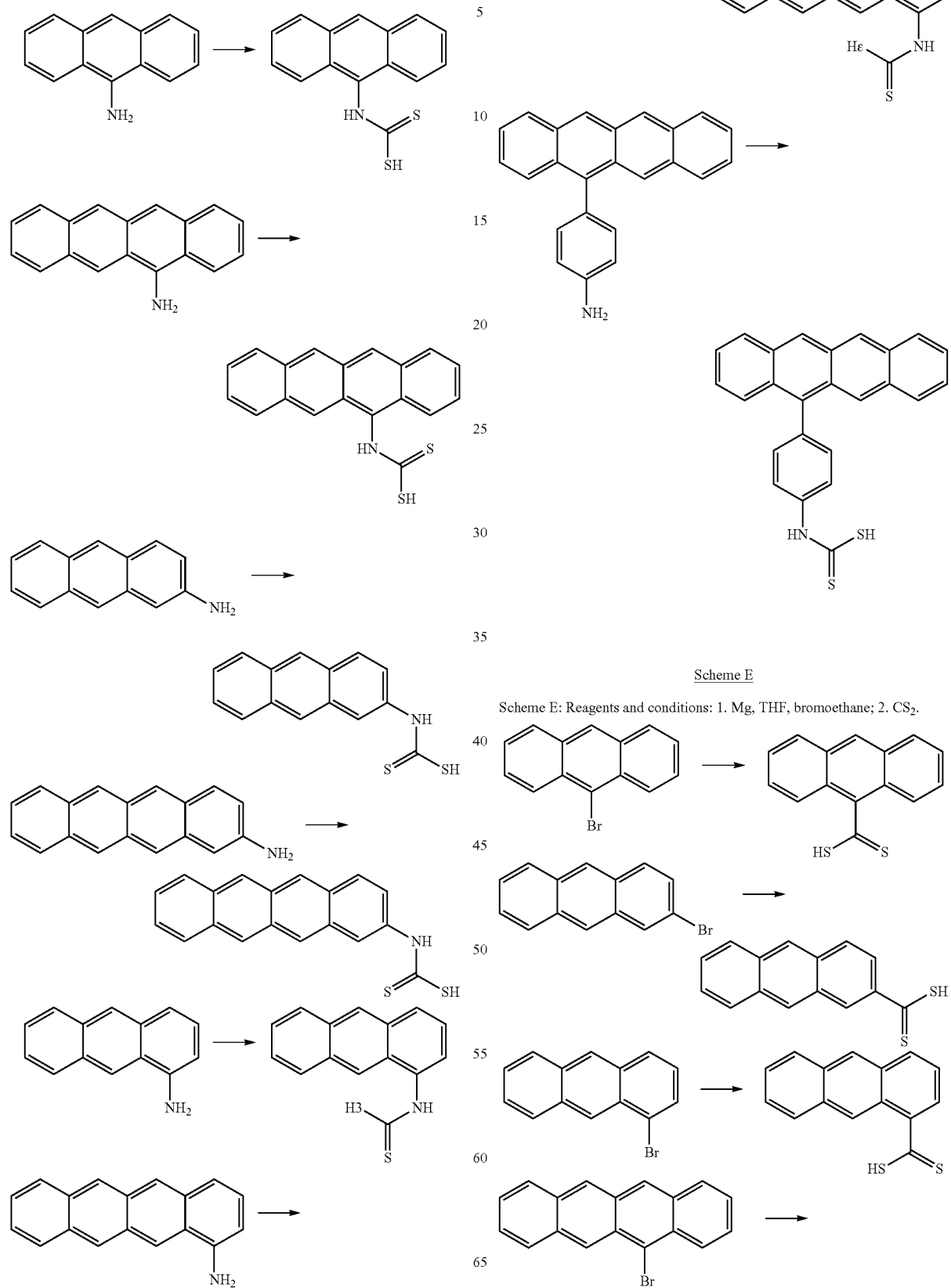

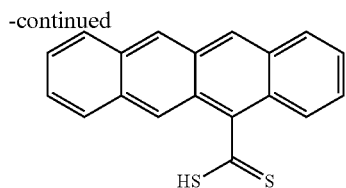

D. Methods for Non-Invasive Bio-Imaging and or Non-Invasive Bio-Detection

As discussed supra, the photon upconversion properties of the nanocrystal transmitter ligand complexes and photon upconversion hybrid systems of the present disclosure make these complexes ideal of non-invasive bio-imaging. The currently described complexes transfer NIR light into the visible spectrum, minimize photodamage and background scattering. Moreover, the low excitation power densities and simultaneous recording of all fluorophores within the field of view addresses current bottlenecks for long-duration imaging of thick tissues, e.g. organs like the brain.

Thus, in another aspect, provided herein are methods of non-invasive bio-imaging and/or non-invasive bio-detection, said method comprising administering to a subject one or more photon upconversion hybrid systems described herein.

In some embodiments, the one or more photon upconversion hybrid systems are incorporated in a nanoemulsion and delivered to an individual. Various methods of producing a nanoemulsion are known in the art.

In some embodiments, the photon upconversion hybrid systems incorporated into a nanoemulsion may be administered locally to the desired site of imaging. In some embodiments, one or more the photon upconversion hybrid systems incorporated into a nanoemulsion further comprise at least one biomolecule. The biomolecule localizes the nanoemulsions to desired imaging areas and eliminates the need for absolute location specific administration.

The biomolecule may be covalently linked to the nanoemulsion or attached via another means known in the art. In some embodiments, one or more components of the nanoemulsion such as a phospholipid, glycol, or phosphitidylcholine of the present invention are modified to incorporate a functional group that provides easy linkage between the nanocrystal transmitter ligand complex and the biomolecule. Known linking chemistries include amid formation, ether formation, etc.

In some embodiments, the biomolecule is a protein, oligopeptide, amino acid, nucleic acid, nucleosides, nucleotides, DNA, hormone, amino acid, peptide, peptidomimetic, RNA, monosaccharide, oligosaccharide, polysaccharide, antibody, lipid, phospholipids, glycolipid or a mixture thereof.

In some embodiments, the biomolecule is an antibody.

In some embodiments, the nanocrystal transmitter ligand complexes are activated with continuous wave light sources at low power densities (~mW/cm$^2$) for optical imaging, phototherapy, fiducial markers and photoacoustic imaging. The visible light produced by photon upconversion in this platform enables wide-field monitoring for long periods of time (i.e. days) with the same start-of-the-art resolution as confocal microscopy. Thus, in some embodiments, the nanocrystal transmitter ligand complexes provide 1, 2, 3, 4, 5, 6, 7 or more days or non-invasive imaging.

In some embodiments, the nanocrystal transmitter ligand complexes provide

Also provided herein is a kit comprising at least one photon upconversion hybrid system described herein. In some embodiments, the kit includes at least one biomolecule. In some embodiments, the kit includes instructions for use.

IV. Examples

Materials & Instrumentation

Chemical reagents were purchased from Acros Organics, Aldrich Chemical Co, Strem, TCI America, or Alfa Aesar and used as received. Specifically, dry and degassed acetone and toluene were obtained from J C Meyer's solvent purification system, HPLC grade hexane was purchased from Fisher Scientific. Cadmium oxide, octadecene and oleic acid were purchased from Alfa Aesar, Aldrich Chemical and TCI America respectively. 9,10-diphenylanthracene (DPA) and 9-anthracenecarboxylic acid (9-ACA) were obtained from TCI America.

Absorption spectra were recorded on a Jasco-V670 UV-Vis absorption spectrophotometer. Fluorescence spectra were recorded on a HORIBA FluoroMax-3 fluorometer. Lasers: A Coherent Sapphire 532 nm laser with an output power of 5.0 mW was used. A 943 W/cm$_2$ 808 nm TO can cw elliptical laser diode (Thor Labs) with the largest and the smallest diameters of 0.12 and 0.06 mm respectively was used for excitation. NMR spectra were recorded on a Varian Inova-400 MHz NMR spectrometer at room temperature. The $^1$H and $^{13}$C Chemical shifts (δ) are reported in parts per million with the residual solvent (CHCl$_3$) peak as an internal standard. Mass spectra were recorded on the Agilent 6210 MS TOF and Agilent LC TOF.

Upconversion fluorescence spectra were recorded from the front face at a 70 degree to the excitation with an Ocean Optics Inc. JAZ spectrometer as shown in FIG. S4. The 808 nm laser is focused by two focal lenses to a spot size of 565.2 μm$^2$. A slit is used to block the unfocused laser. In front of the detector, a 790 nm blocking edge BrightLine® multiphoton short-pass emission filter (part number FF01-790/SP-25) and 532 nm StopLine® single-notch filter (part number NF01-532U-25) are used to block the scattered laser light. The upconverted light was collected from the front of the cuvette and focused by a 30 mm focal lens to the A PAF-SMA11-A (Thor Labs) fiberport through an Ocean Optics QP400-2-SR fiber connected to a JAZ spectrometer. The upconversion sample is in 100 μm or 200 μm thick capillary tubes (Friedrich & Dimmock, Inc. with part numbers of LRT-010-2-10 and LRT-020-4-15 respectively) in air tight Starna cuvettes with screw tops.

The photoluminescence (PL) of nanocrystals (NC) was collected from the front of the cuvette (at right angles from the excitation beam). An Edmund Optics-FC10650836 dichroic mirror was used to collect NC PL. The NC PL was focused on an Ocean Optics QP400-2-VIS-NIR fiber with a 25.4 mm focal length N-BK7 plano-convex lens on a NIRS-0900-1700 Bayspec fluorometer. The upconversion measurement setup is shown in FIG. 1.

Example 1: Synthesis of PbS and PbSe Nanocrystals

Synthesis of 2.9 nm PbS NCs

PbS quantum dots were synthesized by modifying a protocol reported by Hines et al. (Colloidal PbS Nanocrystals with Size-Tunable Near-Infrared Emission: Observation of Post-Synthesis Self-Narrowing of the Particle Size Distribution. *Advanced Materials* 2003, 15, 1844.) 50 PbO (0.45 g), oleic acid (OA, 2 mL), and 1-octadecene (ODE, 18 mL) were mixed in a 50 ml threeneck flask and heated to 110° C. under vacuum for an hour. Pb oleate is formed, indicated by the discoloration of the reaction to a clear solution. Then the reaction atmosphere was switched to Ar, and reaction temperature was set to 78° C. The sulfide precursor, containing 0.21 mL of bis(trimethylsilyl)sulfide in 10 mL of anhydrous ODE, was injected, and the temperature dropped to about 68° C. Immediately after injection, the heater was turned off. After 105 seconds the reaction solution were cooled with compressed air and the injection of 10 ml Hexane. The PbS NCs were transferred to a glovebox and washed 3 times by adding 1:1 hexanes/ethanol mixture; followed by centrifuging at 7000 rpm for 5 min. The supernatant was discarded. The final pellet was dissolved in hexane and stored in the dark inside the glovebox for future use. The PbS NC size (2.9 nm diameter) was determined by measuring the energy of the first exciton peak. The concentration of the PbS NCs was determined from the absorption at 400 nm. The size and the concentration of PbS NCs were determined by measuring the energy of the first exciton peak and the absorption at 400 nm respectively.

Synthesis of 2.5 nm PbSe NCs

PbSe quantum dots were synthesized via a modified protocol reported by Ma et al. (Photovoltaic Performance of Ultrasmall PbSe Quantum Dots. ACS Nano 2011, 5, 8140.) PbO (0.23 g), oleic acid (OA, 3.5 mL), and 1-octadecene (ODE, 10 g) were mixed in a 50 ml threeneck flask and heated to 100° C. under vacuum for an hour. The solution was then heated for an additional 1 h to 150° C. under argon, resulting in a clear, colorless solution. The temperature was reduced to 130° C. The sulfide precursor, containing 62 µl of bis(trimethylsilyl)sulfide in 4 mL of anhydrous ODE, was injected, and the temperature dropped to about 120° C. Immediately after injection, the heater was turned off. After 105 seconds the reaction solution were cooled with compressed air and the injection of 10 ml Hexane. The PbSe NCs were transferred to a glovebox and washed 3 times by adding 1:1 hexanes/ethanol mixture; followed by centrifuging at 7000 rpm for 5 min. The supernatant was discarded. The final pellet was dissolved in hexane and stored in the dark inside the glovebox for future use. The size of the PbSe NCs was determined by measuring the first exciton peak of the absorption spectrum, and the concentration was determined from the calculated size of the PbSe NCs and the absorption at 400 nm.

Example 2: Synthesis of Transmitter Ligand

Synthesis of ethyl 4-(tetracen-5-yl)benzoate (2)

To a mixture of 5-Bromo-tetracene (1) (0.5 g, 1.63 mmol), 4-(ethoxycarbonyl)phenylboronic acid (380 mg, 1.96 mmol, 1.2 mol amt.), cesium carbonate (2.12 g, 6.53 mmol, 4 mol amt.), toluene (19.4 ml) and $H_2O$ (6.536 ml) were added. The reaction was bubbled under argon for 20 min, followed by the addition of 1,1' Bis diphenylphosphino-ferrocene-palladium(II)dichloride dichloromethane complex (133.4 mg, 0.1634 mmol, 0.1 mol amt.) the mixture was then stirred at 60° C. overnight. The reaction was cooled then washed with $H_2O$, and extracted with ethyl acetate four times. The organic layer was washed with brine, dried with magnesium sulfate, filtered and then concentrated using the rotary evaporator. The crude product was purified by flash column chromatography using silica gel and dichloromethane as the eluent to give an orange powder with 61% yield. $^1$H NMR (400 MHz, CDCl$_3$): δ 1.49 (t, 3H), 4.52 (q, 2H), 7.42-7.31 (m, 4H), 7.62-7.57 (m, 3H), 7.80 (d, 1H), 7.99 (d, 1H), 8.06 (d, 1H), 8.20 (s, 1H), 8.34 (d, 2H), 8.72 (s, 1H), 8.76 (s, 1H) ppm. $^{13}$C NMR (400 MHz, CDCl$_3$): δ 14.61, 61.32, 125.05, 125.28, 125.43, 125.61, 125.66, 126.50, 126.72, 127.41, 128.10, 128.76, 128.79, 129.11, 129.53, 129.90, 129.91, 130.01, 130.05, 131.22, 131.36, 131.77, 135.72, 144.23, 166.84 ppm; HRMS (ESI) Calcd. For $C_{27}H_{20}O_2$(MH+) 377.1536, Found 377.1551.

Synthesis of 4-(tetracen-5-yl)benzoic acid (3) (CPT)

To a suspension of ethyl 4-(tetracen-5-yl)benzoate (2) (0.5 g, 1.32 mmol) in 154.4 ml of tetrahydrofuran-methanol (1:1), 3.32 ml of a 2M KOH aqueous solution was added. The mixture was then bubbled for 20 min under argon, then allowed to reflux for 3 hours. THF was removed and the resulting suspension was acidified with 2M of HCl. The crude solid was filtered and washed with $H_2O$ then hot chloroform to give the desired product (orange powder) at 64% yield. $^1$H NMR (400 MHz, DMSO): δ 7.29-7.42 (m, 4H), 7.61 (d, 1H), 7.68 (d, 2H), 7.82 (d, 1H), 8.08 (d, 2H), 8.21 (s, 1H), 8.42 (d, 2H), 8.73 (s, 1H), 8.79 (s, 1H) ppm. $^{13}$C NMR (400 MHz, DMSO): δ 125.05, 125.76, 126.34, 126.35, 126.72, 127.42, 127.94, 128.52, 128.94, 129.13, 129.31, 129.46, 129.97, 130.40, 130.97, 131.30, 131.43, 131.83, 132.11, 132.14, 135.80, 143.61, 167.96 ppm. HRMS (ESI) Calcd. for $C_{25}H_{16}O_2$ (M*+) 348.1145, Found 348.1160.

Example 3: Upconversion Sample Preparation for Upconversion QY Measurement (General Sample Preparation)

Ligand Exchange 2.9 nm PbS with 4-(tetracen-5-yl)benzoic Acid (3), CPT 51.3 µL of PbS/THF (194.8 µM), 150 µL (3)/toluene (1 mM), and 803.5 pt of toluene was mixed leading to a final concentration of [PbS]=10 µM, [5-TetBT]=150 µM. The mixture was stirred for 40 min. Then, 0.3 mL of this ligand exchange solution was transferred into 15 mL centrifuge tube followed by adding 2.4 mL acetone. The resulting solution was centrifuged for 5 min at 7830 rpm. The clear supernatant was removed and the pellet was redispersed into 0.3 mL of 20 mM rubrene/toluene solution. 150 uL of this upconversion solution was transferred to 1 cm*1 cm path length Starna cuvettes containing 100 µm thick borosilicate capillary tube sticking on the wall. The solution will diffuse up through the space inside the capillary tube. Samples were prepared in an argon glovebox.

Ligand Exchange of 2.5 nm PbSe with CPT (3)

Similar to the procedure described above. In the ligand exchange solution, [PbSe]=29 µM, and [3]=150 µM. The resulting solution was stirred for 5 min.

Preparation of PbS+Rubrene and PbSe+Rubrene Control Sample

The desired volume of PbS/PbSe stock solution was measured out, and the solvent was evaporated in the glovebox before adding 0.3 mL of 20 mM rubrene/toluene solution.

Example 4: Calculation of Upconversion Quantum Yield

The upconversion quantum yield is calculated by equation S1 and S2, with rubrene/toluene sample as the reference excited at 532 nm. Both 532 and 808 laser beams are aligned to hit the same position on the sample.

$$\Phi_{UC} = 2\Phi_{ref} \times \frac{\text{(photons absorbed by reference)}}{\text{(photons absorbed by } UC \text{ sample)}} \times \frac{\text{signal}(UC \text{ sample})}{\text{signal(reference)}} \quad (S1)$$

$$\text{photons absorbed/s} = \frac{\text{Laser Power}}{hc/\lambda}(1 - 10^{-Abs}) \quad (S2)$$

$\Phi_{ref}$ is the quantum yield of rubrene and is 0.98, h is Planck's constant, c is the speed of light, and Abs is the sample absorption.

Example 5: Optical Experiment

The instrumentation used for upconversion experiments is discussed above and shown in FIG. 1.

Figure 2:
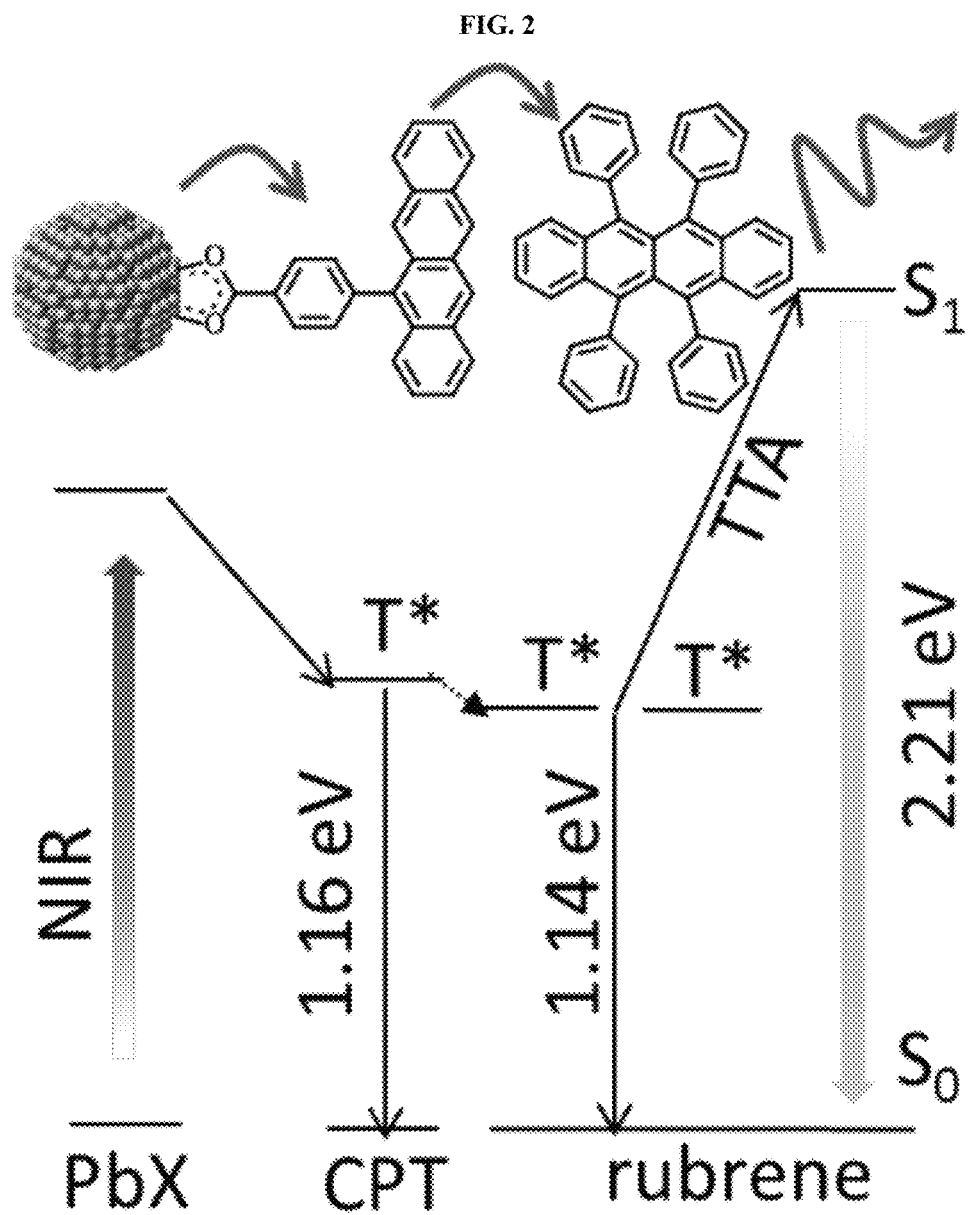
FIG. 2 shows a schematic of energy transfer during upconversion.
Figure 3:
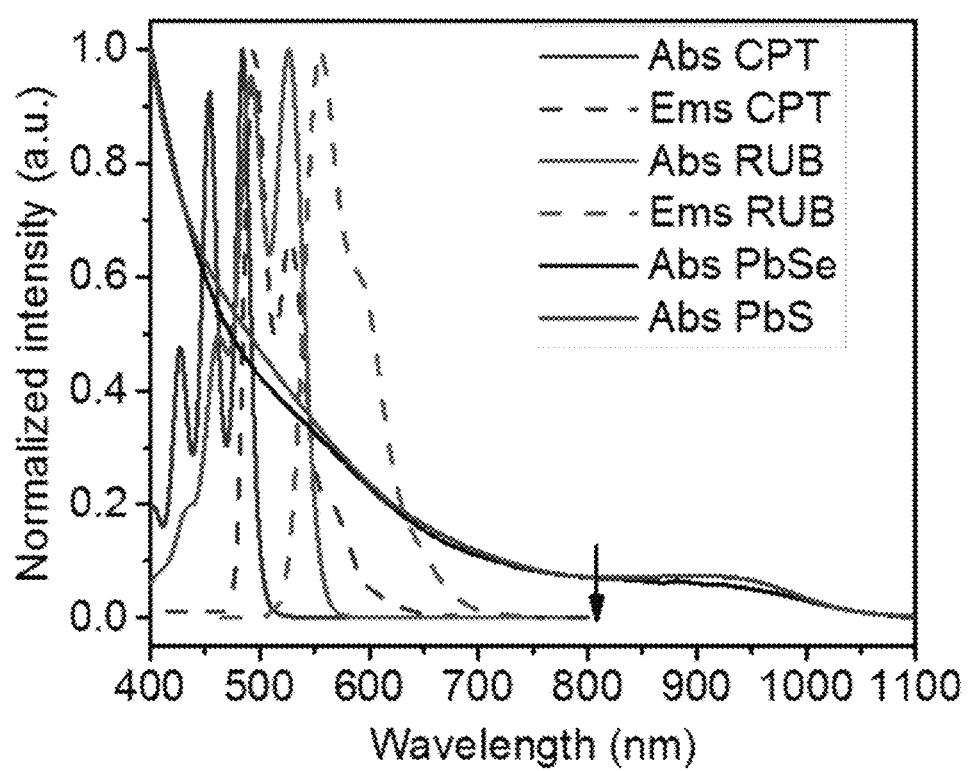
FIG. 3 shows an adsorption and emission spectra of (3), rubrene (dark cyan), 2.9 nM PbS (red), and 2.5 nm PbSe (black) in toluene at room temperature, with excitation wavelength (808 nm) indicated by the black arrow

The components of this hybrid photon upconversion system and their optical properties are shown in FIG. 2. The first step in this upconversion scheme occurs when PbX NCs absorb a NIR photon (red arrow). Triplet energy transfer (TET) is enhanced in the presence of CPT (3) directly anchored on the NC surface. TET subsequently occurs between CPT and rubrene in solution. Two rubrene molecules then undergo TTA to emit a visible photon at 570 nm (yellow arrow). Here, a CPT scaffold is chosen as the transmitter because its Ti energy level is a little larger (1.16 eV, estimated from triplet energy of 5-phenyltetracene) than that of rubrene, thus forming a cascade for directional energy transfer. The absorption and emission spectra of the PbX NCs, CPT, and the rubrene annihilator are shown in FIG. 3. CPT has a fluorescence QY of 0.53 and an extinction coefficient of 9340 M$^{-1}$cm$^1$ at its absorption maxima of 484 nm. Optical properties of upconversion are shown in Table 1.

TABLE 1

Optical properties of upconversion transmitter CPT (3) and rubrene

| | $\lambda_{max}$ (Abs.) (nm) | $\lambda_{max}$ (Em.) (nm) | $\varepsilon @ \lambda_{max}$ (M$^{-1}$ cm$^{-1}$) | Quantum yield(%) |
|---|---|---|---|---|
| CPT | 484 | 494 | 9340 | 53.1 |
| rubrene | 526 | 556 | 12000 | 98.0 |

Figure 4:
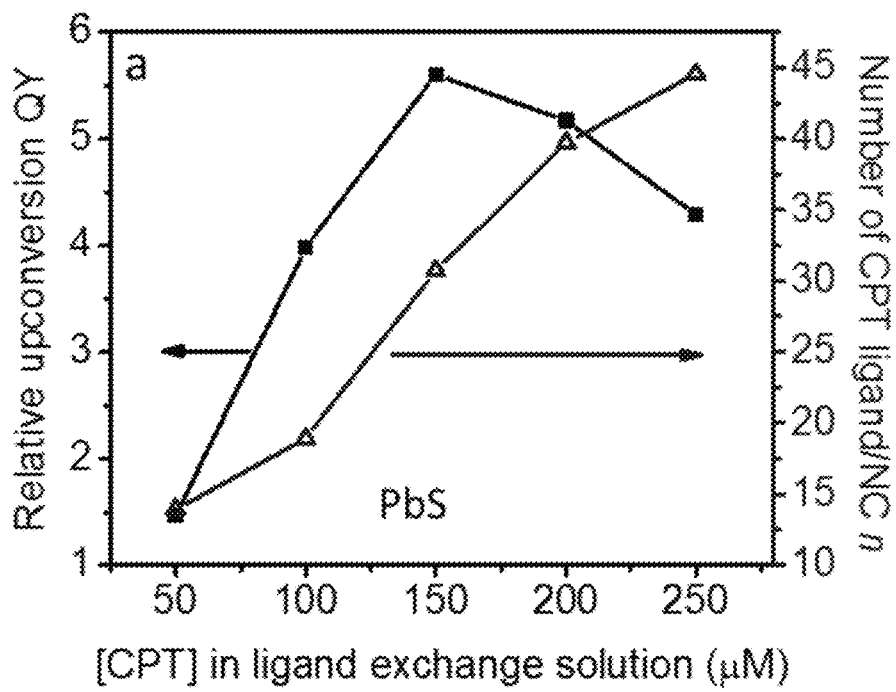
FIG. 4 shows a plot of the relative upconversion QY where the upconversion fluorescence intensity normalized by the absorption at the excitation wavelength of 808 nm (black squares), and the number of bound CPT transmitter ligands per NC (hollow blue triangles) for PbS NC versus [CPT] in ligand exchange solution. The sample contains 1 mM rubrene and was measured in 200 μm thick capillary tube sealed in Starna cuvettes. Ligand exchange condition: PbS: stirring 10 μM PbS with CPT in designated concentration for 40 min.
Figure 5:
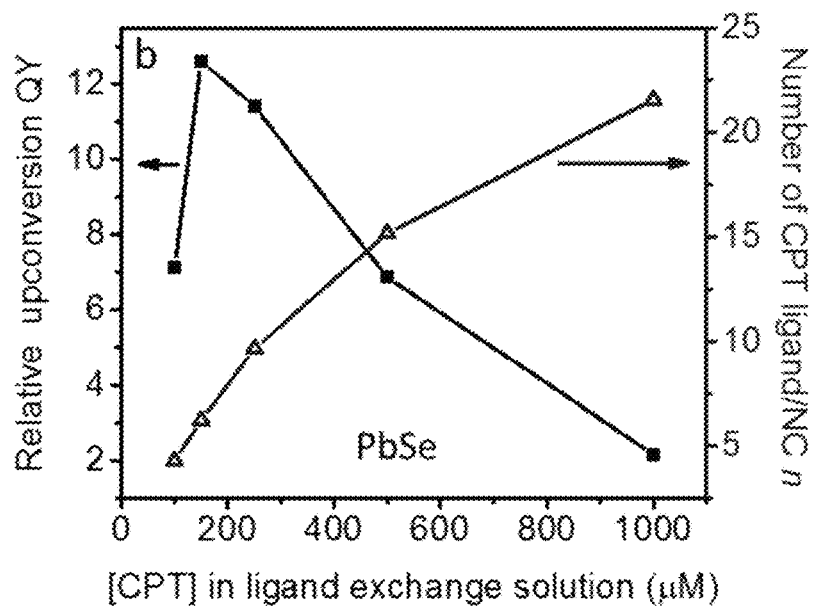
FIG. 5 shows a plot of the relative upconversion QY where the upconversion fluorescence intensity normalized by the absorption at the excitation wavelength of 808 nm (black squares), and the number of bound CPT transmitter ligands per NC (hollow blue triangles) for PbS NC versus [CPT] in ligand exchange solution. The sample contains 1 mM rubrene and was measured in 200 μm thick capillary tube sealed in Starna cuvettes. Ligand exchange condition: PbSe: stirring 29 μM PbSe with CPT in designated concentration for 20 min.

As shown in FIG. 4 and FIG. 5, for both PbS (FIG. 4) and PbSe (FIG. 5), the number of CPT transmitter ligands bound per particle, n, correlates positively with the concentration of CPT in the ligand exchange solution (denoted as $[CPT]_{LX}$). For 2.9 nm diameter PbS NCs, n varies from 14 to 45 as $[CPT]_{LX}$ is increased from 50 to 250 µM. The corresponding transmitter ligand density increases from 0.53 to 1.7 nm$^{-2}$. In comparison, there are 3 to 22 CPT ligands per 2.5 nm diameter PbSe NCs when $[CPT]_{LX}$ increases from 100 to 1000 µM, with ligand density ranging from 0.22 to 1.1 nm$^{-2}$. The correlation between $[CPT]_{LX}$ and n was also confirmed by the photoluminescence (PL) quenching of 2.9 nm PbS. As shown in FIG. S1, the PL of PbS was quenched with increasing $[CPT]_{LX}$ ranging from 100 to 1500 µM. This estimate for n is obtained from the UV-Vis absorption spectrum of the PbX/CPT complex that does not contain free ligand, taking into account the extinction coefficients of both the molecule and NC, assuming no charge transfer occurs. It is described in detail in the SI. The number of CPT transmitter ligands bound affects the solubility of the PbX/CPT complex. Experimentally, it was impossible to redisperse the PbX-CPT pellet in toluene after centrifugation if $[CPT]_{LX}$ exceeded 1500 µM, and the PbX NCs would even spontaneously crash out of solution if $[CPT]_{LX}$ was over 2000 µM. Since CPT can effectively displace the native oleic acid ligands on the PbX NCs, the functionalized NCs no longer remain soluble if complete ligand exchange occurs. This is expected when the solubilizing long-chain hydrocarbons on the NC surface are completely replaced with the relatively insoluble CPT. The original oleic acid capped PbS and PbSe NCs have their surface saturated with carboxylic acid ligands with ligand densities of 3.0 and 4.2 nm$^{-2}$ respectively.

The surface densities of CPT on PbS and PbSe NCs that lead to aggregating structures are 0.75 and 1.1 nm$^{-2}$ respectively, consistent with the fact that the CPT molecule is around 4 times wider than oleic acid. Since the goal of this work is to establish ligand enhanced upconversion of NIR photons in solution, we used $[CPT]_{LX}$ below 1500 µM, where the PbS/CPT complex remains soluble. We found the upconversion QY reaches a maximum and then decreases as the number of bound transmitter ligands is increased (FIG. 4 and FIG. 5). Here, the relative upconversion QY is the upconversion fluorescence intensity of the rubrene emitter at 560 nm normalized by the absorption of the PbX NC at 808 nm. In FIGS. 2a and b, both PbS and PbSe sensitized upconversion show the highest relative QY at the optimal $[CPT]_{LX}$ of 150 µM. Since more CPT ligand is bound when $[CPT]_{LX}$ is higher, the diminished upconversion at higher ligand loadings suggests that TET from CPT to free rubrene in solution is compromised. This suggests that the TTA process may be occurring between two neighboring CPT molecules where newly introduced ligands may be aggregating together on the NC surface, as opposed to being randomly distributed. On the other hand, emission from the singlet state of surface bound CPT may be quickly quenched due to rapid Förster energy transfer to the NC acceptor. For isolated CPT, energy transfer to free rubrene avoids quenching by the NCs.

Figure 6:
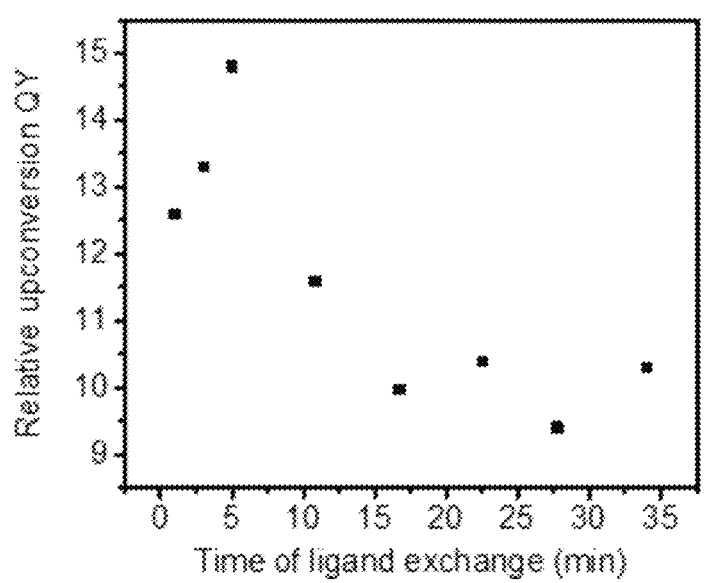
FIG. 6 shows the relative upconversion quantum yield (upconversion fluorescence intensity at 560 nm normalized by the absorption at 808 nm) of PbSe/CPT/rubrene samples for different ligand exchange times. Ligand exchange conditions: 29 μM PbSe, 150 μM CPT, stirring in toluene at RT. Samples contain 1 mM rubrene, and were measured in 200 μm thick capillary tube sealed in air tight Starna cuvettes
Figure 7:
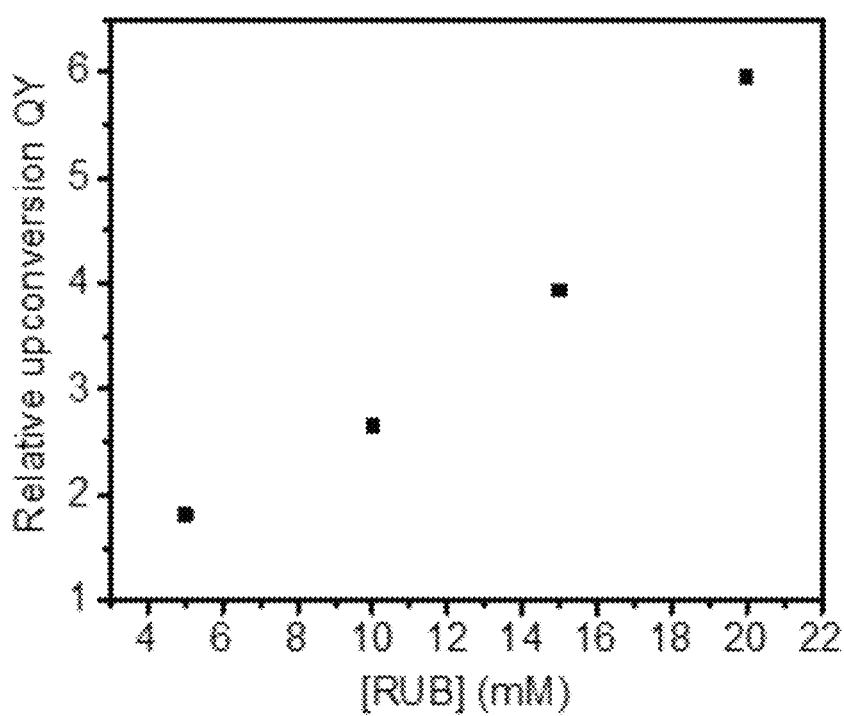
FIG. 7 shows the relative upconversion quantum yield (upconversion fluorescence intensity at 560 nm normalized by the absorption at 808 nm) of PbS/CPT/rubrene samples containing different concentrations of rubrene. Ligand exchange condition: 10 μM PbS, 1 mM CPT, and stirring in THF for 1 h. Samples were measured in 200 μm thick capillary tube sealed in air tight Starna cuvettes.
Figure 8:
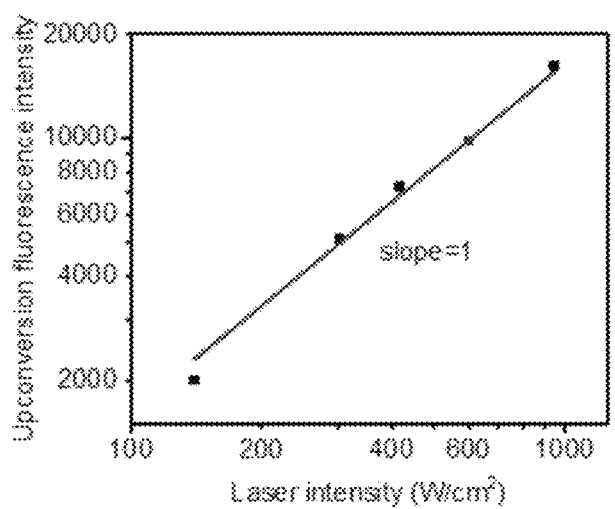
FIG. 8 shows a log-log plot of the upconversion signal versus laser intensity for the 2.9 nm PbS/CPT/rubrene sensitizer/ligand/emitter system, showing the laser intensity in use is in linear (slope=1) regime. Ligand exchange conditions: 10 μM PbS, 1 mM CPT, stirring in THF for/10 min. The sample cotain 1 mM rubrene, and was measured in 100 μm thick capillary tube sealed in air tight Starna cuvettes

To realize the maximum upconversion QY, other parameters such as the duration of ligand exchange, concentration of rubrene, and measurement setup was optimized. Other than $[CPT]_{LX}$, n can also be controlled with the time allowed for ligand exchange. FIG. 6 shows the correlation between 2.5 nm PbSe sensitized upconversion QY and ligand exchange time. With 29 µM PbSe and a fixed 150 µM of $[5\text{-CPT}]_{LX}$ in the ligand exchange solution, the highest upconversion efficiency was obtained after 5 min of stirring. A shorter or longer ligand exchange time leads to insufficient or too many CPT ligands per PbSe NC respectively. The upconversion quantum efficiency plateaus when the ligand exchange time exceeds 15 min, indicating that equilibrium is achieved. The upconversion QY increases with the concentration of rubrene, as shown in FIG. 7, in accordance with reports in molecular visible upconversion systems. As shown in FIG. 2, a high upconversion QY relates to efficient triplet energy transfer from CPT to rubrene, and the TTA between two rubrene molecules. The higher the concentration of rubrene, the more triplet rubrene formed, the higher the upconversion QY. Finally, to minimize the parasitic reabsorption of the upconversion signal by the NCs, the sample was put in a capillary tube with a thickness of 100 µm and sealed in an air free 1 cm by 1 cm path length cuvette. The upconversion signal was measured in a front face geometry (see FIG. 1). Excitation power density dependence measurements were performed to confirm that all measurements occurred in the linear regime (FIG. 8).

Example 6: Synthesis of Transmitter Ligand

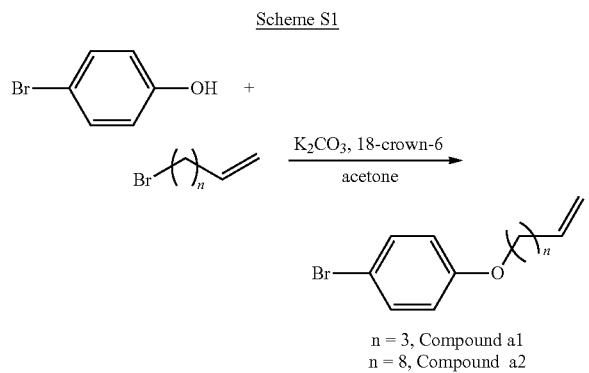

Scheme S1 n = 3, Compound a1
n = 8, Compound a2

4-bromophenol (3.0 g, 20.1 mmol, 1.0 eq), 5-bromo-1-pentene (3.0 g, 20.1 mmol, 1.0 eq), potassium carbonate (3.47 g, 25.1 mmol, 1.25 eq), potassium iodide (0.53 g, 2.01 mmol, 0.1 eq), 18-crown 6 (0.334 g, 2.01 mmol, 0.1 eq) and 100 mL acetone were mixed in two neck reaction flask. The solution refluxed for 12 h until the reaction was done. After cooling down to room temperature and removing the solvent under reduced pressure, the solution was extracted with $CH_2Cl_2$ and washed with water several times. The organic layer was then dried with $MgSO_4$, and the solvent was removed with a rotary evaporator. The resulting crude product was purified by silica gel column chromatography to get rid of excess 18-crown-6. A colorless oil of 3.34 g was obtained (70% yield). $^1$H NMR (400 MHz, CDCl$_3$): δ=7.34 (d, 2H, J=9.0 Hz), 6.78 (d, 2H, J=9.0 Hz), 5.83 (m, 1H), 5.02 (m, 2H), 3.93 (t, 2H), 2.22 (m, 2H), 1.87 (m, 2H) ppm.

Compound a2 was obtained in the same way as compound a1 as 3.17 g of a colorless oil (yield 74%). $^1$H NMR (400 MHz, CDCl$_3$): δ=7.34 (d, 2H, J=9.0 Hz), 6.78 (d, 2H, J=9.0 Hz), 5.80 (m, 1H), 4.95 (m, 2H), 3.91 (t, 2H), 2.03 (m, 2H), 1.76 (m, 2H), 1.31 (m, 10H) ppm. The proton NMR matches the reported value.

Oxidation

The oxidation of compound a1 and compound a2 was performed following a method by Travis, B. R.; Narayan, R. S.; Borhan, B. Journal of the American Chemical Society 2002, 124, 3824

Scheme S2

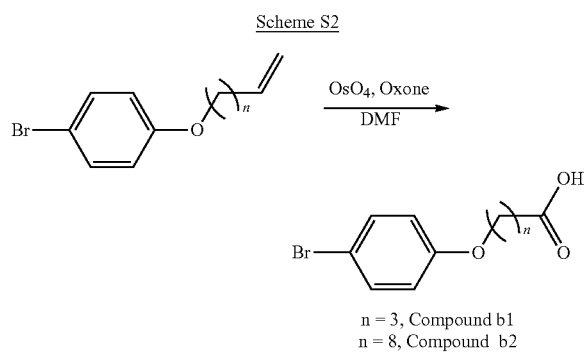

n = 3, Compound b1
n = 8, Compound b2

Compound b1: Compound 1a (3.0 g, 12.4 mmol, 1.0 eq) was dissolved in 62 mL DMF (0.2 M), and 1.6 mL OsO$_4$ (0.01 eq, 2.5% in tBuOH) was added and stirred for 5 min. Oxone® (15 g, 49.6 mmol, 4.0 eq) was added in one portion and the reaction was stirred at RT for 8 h. Na$_2$SO$_3$ (100 mg, 6.0 eq w/w) was added, to reduce the remaining Os(VIII), and stirred for an additional hour. The final solution would became dark brown/black. EtOAc was added to extract the products and 1N HCl was used to dissolve the salts. The organic extract was washed with 1N HCl (3×) and brine, dried over MgSO$_4$, and the solvent was removed under reduced pressure to obtain the crude product. Products were purified by silica gel column chromatography to give 2.3 g of a white solid (70%). $^1$H NMR (400 MHz, CDCl$_3$): δ=7.38 (d, 2H, J=9.0 Hz), 6.78 (d, 2H, J=9.0 Hz), 3.99 (t, 2H), 2.58 (m, 2H), 2.12 (m, 2H) ppm. $^{13}$C NMR (500 MHz, CDCl$_3$): δ=178.97, 157.96, 132.38, 116.39, 113.09, 66.87, 30.53, 24.39 ppm. HRMS (–ESI/APCI) (mass m/z): 256.9829 [M–H]$_-$.

Compound b2 was obtained in the same way as compound b1 using compound a2 instead. A white solid was isolated (1.4 g, 63%). $^1$H NMR (400 MHz, CDCl$_3$): δ$_H$=7.34 (d, 2H, J=9.0 Hz), 6.78 (d, 2H, J=9.0 Hz), 3.91 (t, 2H), 1.76 (m, 2H), 1.64 (m, 2H), 1.35 (m, 10H) ppm. $^{13}$C NMR (500 MHz, CDCl$_3$): δ$_C$=179.51, 158.35, 132.32, 116.43, 112.71, 68.33, 34.06, 29.55, 29.42, 29.27, 29.09, 26.07, 24.77 ppm. HRMS (–ESI/APCI) (mass m/z): 329.0639 [M*]$_-$.

Suzuki Coupling

Compound c1 and c2 were synthesized following a method by Ishiyama, T.; Murata, M.; Miyaura, N. The Journal of Organic Chemistry 1995, 60, 7508.

Scheme S3

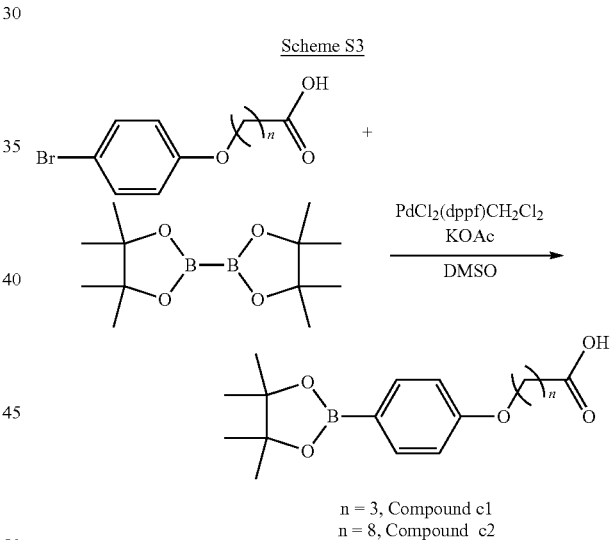

n = 3, Compound c1
n = 8, Compound c2

Compound c1: Compound b1 (2 g, 7.7 mmol, 1.0 eq), bis(pinacolato)diboron (2.2 g, 9.0 mmol, 1.1 eq), KOAc (4.5 g, 46.3 mmol, 6.0 eq), 48 mL DMSO are mixed in a flask. The reaction was degassed under Ar for 20 min and then Pd(dppf)Cl$_2$.CH$_2$Cl$_2$ (0.085 g, 0.1 mmol, 0.03 eq) was added under high argon flow. The reaction was heated at 80° C. for 8 hours. After cooling to room temperature, the reaction was extracted with EtOAc and washed with brine several times. The organic layer was then dried with MgSO$_4$, and the solvent was removed with a rotary evaporator. The resulting crude product was purified by silica gel column chromatography and EtOAc:hexane=1:1 as the eluent. A pale yellow solid was obtained after removal of the solvents (1.7 g, 73% yield). $^1$H NMR (400 MHz, CDCl$_3$): δH=7.58 (d, 2H, J=9.0 Hz), 6.93 (d, 2H, J=9.0 Hz), 3.99 (t, 2H), 2.37 (m, 2H), 1.93 (m, 2H), 1.27 (s, 12H) ppm. $^{13}$C NMR (500 MHz, CDCl$_3$):

δC=178.97, 161.46, 136.65, 113.95, 105.13, 83.70, 66.42, 30.58, 25.15, 24.98 ppm. HRMS (+ESI/APCI) (mass m/z): 307.1706 [M+H]+

Compound c2 was obtained in the same way as compound c1 using compound b2 instead to give a white solid (0.88 g, 67% yield). $^1$H NMR (400 MHz, CDCl$_3$): $TM_H$=7.72 (d, 2H, J=9.0 Hz), 6.87 (d, 2H, J=9.0 Hz), 3.97 (t, 2H), 1.76 (m, 2H), 1.64 (m, 2H), 1.35 (m, 10H), 1.26 (s, 12H) ppm. $^{13}$C NMR (500 MHz, CDCl$_3$): $TM_C$=179.55, 161.79, 136.55, 113.93, 105.07, 83.59, 67.78, 34.02, 29.23, 29.04, 26.03, 25.10, 24.92, 24.72, 24.61 ppm. HRMS (+ESI/APCI) (mass m/z): 309.2325 [M+Na]+.

purified by silica gel column chromatography to yield 45.6 mg pale yellow solid (32% yield). $^1$H NMR (400 MHz, CDCl$_3$): $TM_H$=8.48 (s, 1H), 8.03 (d, 2H, J=8.4 Hz), 7.69 (d, 2H, J=8.8 Hz), 7.46 (m, 2H), 7.35 (m, 4H), 7.12 (d, 2H, J=8.3 Hz), 4.18 (t, 2H), 2.70 (t, 2H), 2.24 (m, 2H) ppm. $^{13}$C NMR (500 MHz, CDCl$_3$): $TM_C$=179.00, 158.32, 136.90, 132.43, 131.52, 131.07, 130.64, 128.43, 127.02, 126.49, 125.34, 125.17, 114.45, 68.06, 30.78, 24.66 ppm. HRMS (−ESI/APCI) (mass m/z): 356.1400 [M*]⁻.

Compound CP9A was obtained in the same way as compound CP4A using compound c2 instead to give a white solid (64 mg, 20% yield). $^1$H NMR (400 MHz, CDCl$_3$): δ$_H$=8.48 (s, 1H), 8.03 (d, 2H, J=8.4 Hz), 7.72 (d, 2H, J=8.8 Hz), 7.46 (m, 2H), 7.33 (m, 4H), 7.12 (d, 2H, J=8.5 Hz), 4.09 (t, 2H), 2.39 (t, 2H), 1.88 (m, 2H), 1.41 (m, 10H) ppm. $^{13}$C NMR (500 MHz, CDCl$_3$): δ$_C$=179.25, 158.71, 137.08, 132.41, 131.55, 130.73, 130.68, 128.44, 127.10, 126.45, 125.32, 125.18, 114.48, 68.19, 34.06, 29.53, 29.37, 29.17, 26.26, 25.76, 24.85 ppm. HRMS (+ESI/APCI) (mass m/z): 427.2340 [M+H]+.

Scheme S4

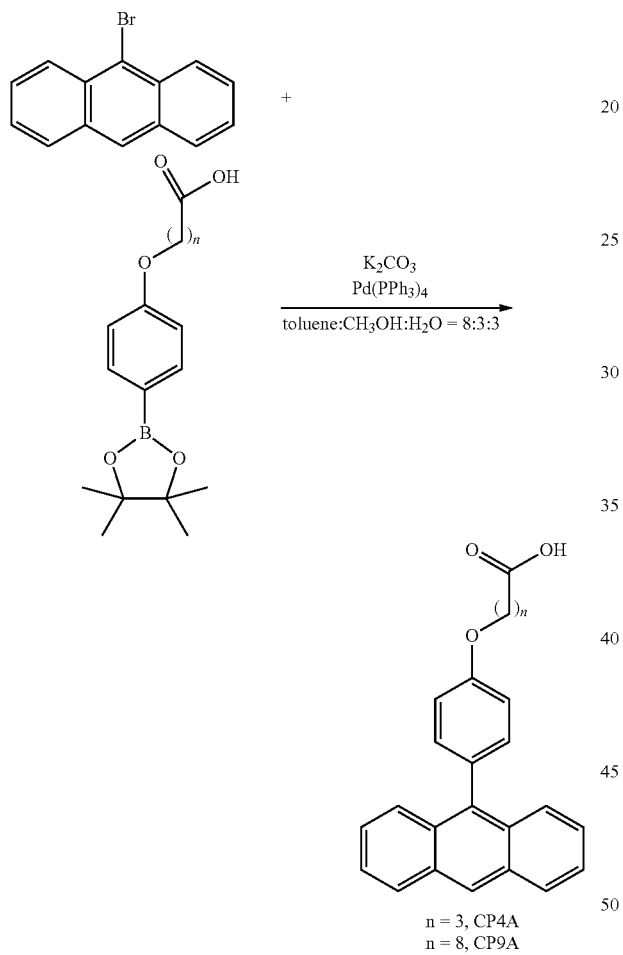

n = 3, CP4A
n = 8, CP9A

Compound CP4A, CP9A, d1 and d2 were synthesized following a method by Shi, D.; Ren, Y.; Jiang, H.; Lu, J.; Cheng, X. Dalton Transactions 2013, 42, 484.

Compound CP4A: A mixture of compound c1 (147.3 mg, 0.40 mmol, 1.0 eq), 9-bromoanthracene (123.4 mg, 0.48 mmol 1.2 eq), K$_2$CO$_3$ (387 mg, 2.8 mmol, 7.0 eq) was placed in a 50 ml schlenk tube and 3.3 ml of degassed of toluene:CH$_3$OH:H$_2$O (8:3:3) were added. After degassing under argon for 20 min, Pd(PPh$_3$)$_4$ (12 mg, 0.0104 mmol, 0.026 eq) was added under argon. After heating to 80° C. under argon atmosphere for 18 h the solvent was removed to give a dark yellow residue. The solid was suspended in water and extracted with EtOAc. After drying the organic phase over MgSO$_4$ and removing the solvent, the product was Scheme S5

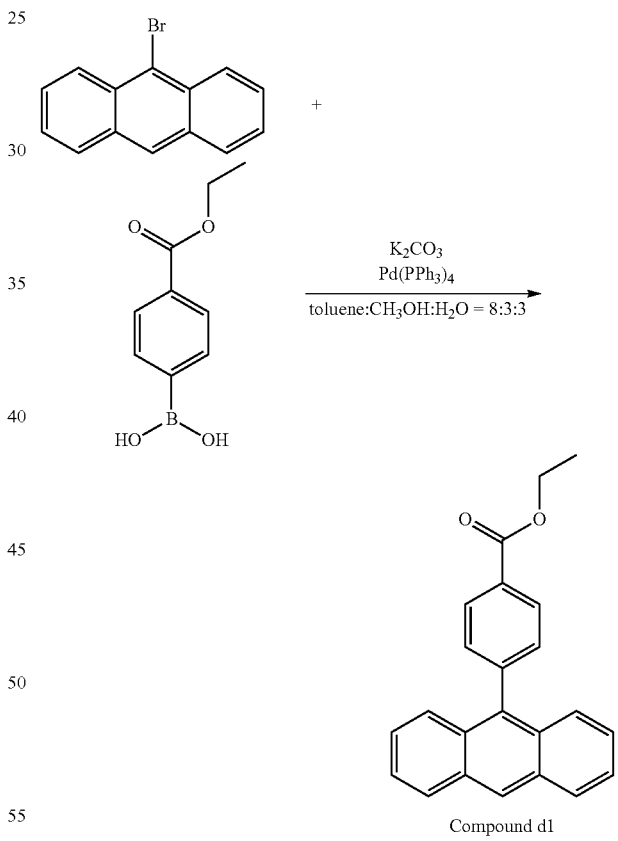

Compound d1

Compound d1: A mixture of 9-bromoanthracene (500 mg, 1.94 mmol), 4-ethoxycarbonylphenylboronic acid (471.5 mg, 2.43 mmol), K$_2$CO$_3$ (938.4 mg, 6.79 mmol) and 16 mL of toluene:CH$_3$OH:H$_2$O (8:3:3) was mixed in a flask. The solution was degassed under argon for 20 min and Pd(PPh$_3$)$_4$ (58.3 mg, 0.05 mmol, 2.5 mol %) was added under high argon flow. The reaction then was stirred under argon for 12 h at 80° C. After the mixture was cooled to room temperature, it was extracted with EtOAc and washed with H$_2$O several times. The organic layer was then dried with MgSO$_4$, and the solvent was removed with a rotary evaporator. The resulting crude product was purified by silica gel column chromatography and CH$_2$Cl$_2$:hexane=5:1 as the eluent. A white solid was obtained (565 mg, 90% yield). $^1$H NMR (400 MHz, CDCl$_3$): δ$_H$=8.53 (s, 1H), 8.26 (d, 2H, J=8.4 Hz), 8.05 (d, 2H, J=8.4 Hz), 7.58 (m, 4H), 7.47 (m, 2H), 7.36 (m, 2H), 4.49 (q, 2H), 1.47 (t, 3H) ppm. $^{13}$C NMR (500 MHz, CDCl$_3$): δ$_C$=167.21, 143.98, 135.84, 131.52, 131.40, 129.98, 129.76, 129.54, 128.57, 127.24, 126.45, 125.82, 125.32, 61.24, 14.57 ppm. HRMS ESI-MS (mass m/z): 327.1367 [M+H]+

Scheme S6

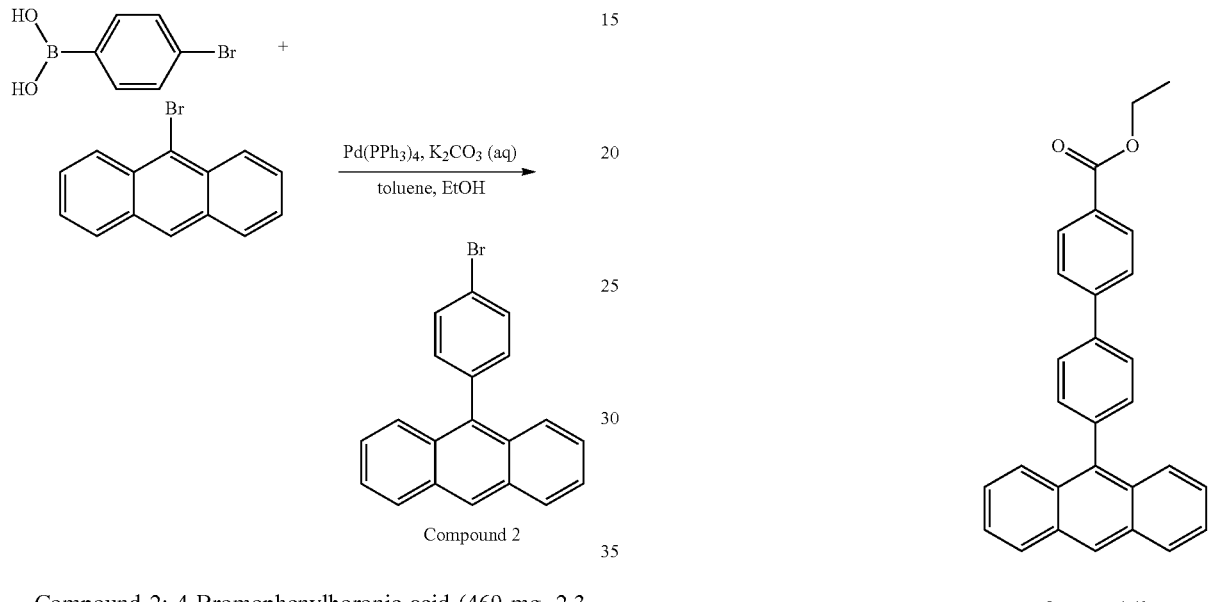

Compound 2

Compound 2: 4-Bromophenylboronic acid (469 mg, 2.3 mmol), 9-bromoanthracene (500 mg, 1.9 mmol), 17.6 mL of dry toluene, and 11.6 mL aqueous of K$_2$CO$_3$ solution (2.0 M) were placed in a 50 mL round-bottom flask. Pd(PPh$_3$)$_4$ (67.2 mg, 0.06 mmol) was added after degassing under argon for 20 min. The mixture was vigorously stirred at 80° C. for 10 hours. After cooling to room temperature, the resulting mixture was extracted with CH$_2$Cl$_2$ followed by purification by column chromatography on silica gel with hexane as the eluent to offer a white solid. The desired compound was obtained in 64% yield (414 mg). $^1$H NMR (400 MHz, CDCl$_3$): δ$_H$=8.51 (s, 1H; Ar H), 8.04 (d, 2H, J=8.3 Hz), 7.71 (d, 2H, J=7.4 Hz), 7.64 (d, 2H, J=9.1 Hz), 7.47 (m, 2H), 7.37 (m, 2H), 7.33 (d, 2H, J=8.8 Hz) ppm. The proton NMR matches the reported value. HRMS (+ESI/APCI) (mass m/z): 333.0269 [M−H]+

Scheme S7

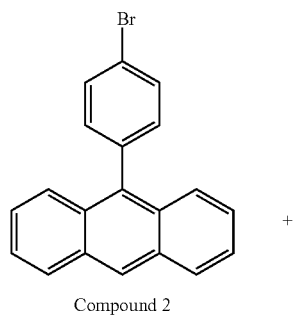

Compound 2

+

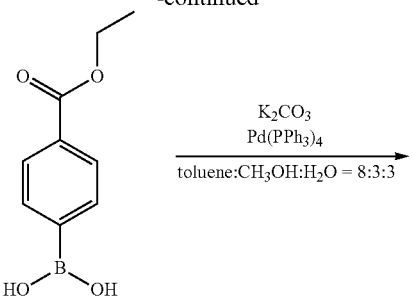

Compound d2

Compound d2: A mixture of compound 2 (277 mg, 0.83 mmol), 4-ethoxycarbonylphenylboronic acid (403 mg, 2.08 mmol), K$_2$CO$_3$ (802 mg, 5.81 mmol) and 7.0 mL of toluene: CH$_3$OH:H$_2$O (8:3:3) was mixed in a flask. The reaction was degassed under argon for 20 min. Then Pd(PPh$_3$)$_4$ (48.0 mg, 0.04 mmol, 5.0 mol %) was added under argon. Then the reaction was stirred under argon for 12 h at 80° C. After the mixture was cooled to room temperature, it was extracted with EtOAc and washed with H$_2$O several times. The organic layer was then dried with MgSO$_4$, and the solvent was removed with a rotary evaporator. The resulting crude product was purified by silica gel column chromatography and CH$_2$Cl$_2$:hexane=1:1 as the eluent. A white solid was obtained (303 mg, 75% yield). $^1$ NMR (400 MHz, CDCl$_3$): δ=8.53 (s, 1H), 8.18 (d, 2H, J=8.5 Hz), 8.06 (d, 2H, J=8.4 Hz), 7.84 (m, 4H), 7.71 (d, 2H, J=8.7 Hz), 7.56 (d, 2H, J=8.3 Hz), 7.48 (m, 2H), 7.37 (m, 2H), 4.43 (q, 2H), 1.45 (t, 3H) ppm. $^{13}$C NMR (500 MHz, CDCl$_3$): δ$_C$=166.68, 145.28, 139.21, 138.91, 136.43, 132.02, 131.50, 130.33, 130.18, 129.04, 128.54, 127.35, 127.14, 126.91, 126.81, 125.62, 125.29, 61.16, 14.55 ppm. HRMS (+ESI/APCI) (mass m/z): 403.1717 [M−H]+.

Ester Deprotection

Ester deprotection was performed via the method published by Ogawa, T.; Yanai, N.; Monguzzi, A.; Kimizuka, N. Scientific Reports 2015, 5, 10882. The synthesis for CPA and CPPA is described below.

Scheme S8

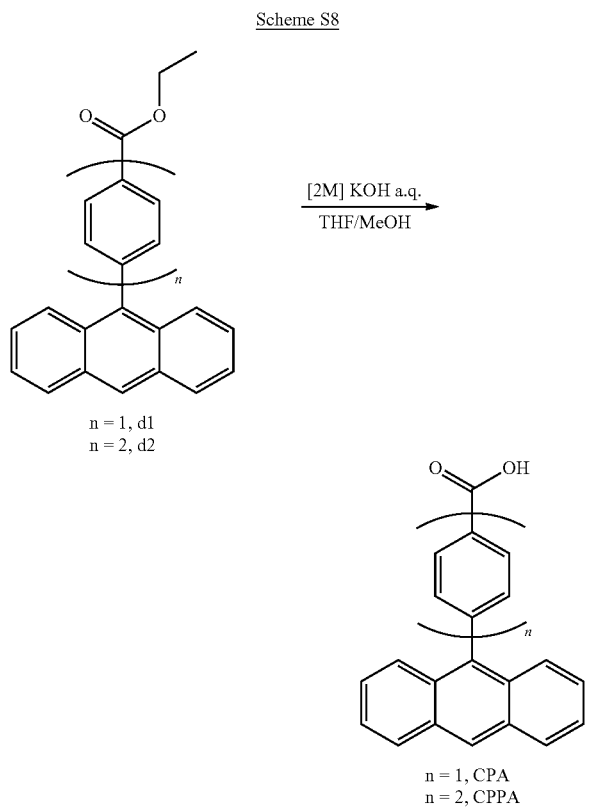

n = 1, d1
n = 2, d2 n = 1, CPA
n = 2, CPPA

Compound CPA: To a solution of 176.3 mg (0.54 mmol) of compound d1 in 54 ml 1:1 mixture of THF-MeOH, 12 ml of a KOH aqueous solution (2M) was added. The mixture was allowed to reflux for 5 h. THF was removed under reduced pressure and the resulting suspension was diluted with water. The precipitate formed by acidification with aqueous HCl (2M) was collected by filtration, washed several times with water yielding 135.3 mg (84%) of a pale yellow solid. $^1$H NMR (400 MHz, CDCl$_3$): $\delta_H$=8.54 (s, 1H), 8.33 (d, 2H, J=8.3 Hz), 8.06 (d, 2H, J=8.6 Hz), 7.59 (m, 4H), 7.48 (m, 2H), 7.37 (m, 2H) ppm. $^{13}$C NMR (500 MHz, CDCl$_3$): $\delta_C$=171.49, 145.13, 136.42, 135.63, 131.77, 131.43, 130.47, 129.97, 128.62, 127.38, 126.43, 125.93, 125.39 ppm. HRMS (−ESI/APCI) (mass m/z): 297.0925 [M−H]$^-$ Compound CPPA: To a solution of 196 mg (0.49 mmol) Compound d2 in 49 ml 2:1 mixture of THF/MeOH, 12 ml of a 2M KOH aqueous solution was added. The mixture was allowed to reflux for 5 h. THF was removed under reduced pressure and the resulting suspension was diluted with water. The precipitate formed by acidification with aqueous HCl (2M) was collected by filtration, washed several times with water. The crude product was recrystallized in CHCl$_3$ and methanol mixture yielding 173.0 mg (95%) of a pale yellow solid. $^1$H NMR (400 MHz, CDCl$_3$): $\delta_H$=8.54 (s, 1H), 8.23 (d, 2H, J=8.3 Hz), 8.06 (d, 2H, J=9.4 Hz), 7.86 (d, 4H, J=8.3 Hz), 7.72 (d, 2H, J=8.8 Hz), 7.58 (d, 2H, J=7.9 Hz), 7.49 (m, 2H), 7.38 (m, 2H) ppm. $^{13}$C NMR (500 MHz, CDCl$_3$): $\delta_C$=170.21, 146.25, 139.17, 139.08, 136.39, 132.10, 131.53, 131.03, 130.33, 128.98, 128.57, 127.45, 127.36, 126.97, 126.82, 125.66, 125.32 ppm. HRMS (−ESI/APCI) (mass m/z): 374.1298 [M*]$_-$

Example 7: Nanocrystal Synthesis

CdSe nanocrystals (NCs) were synthesized and purified by the procedure published by Carbone, L.; Nobile, C.; De Giorgi, M.; Sala, F. D.; Morello, G.; Pompa, P.; Hytch, M.; Snoeck, E.; Fiore, A.; Franchini, I. R.; Nadasan, M.; Silvestre, A. F.; Chiodo, L.; Kudera, S.; Cingolani, R.; Krahne, R.; Manna, L. Nano Letters 2007, 7, 2942. Trioctylphosphine oxide (TOPO) (3.0 g), octadecylphosphonic acid (ODPA) (0.280 g) and CdO (0.060 g) were mixed in a 25 mL three neck flask, heated to ca. 150° C. and exposed to vacuum for 1 hour. Then, under Ar (g), the solution was heated to about 330° C. to dissolve the CdO. At this point, 1.5 g of trioctylphosphine (TOP) was injected and the temperature was increased to 370° C. Then the Se:TOP solution (0.058 g Se+0.360 g TOP) is injected. About 10 s after injection, the reaction flask was cooled down quickly with compressed air. After the synthesis, as-prepared CdSe NCs were transferred to the glove box and cleaned with methanol and toluene at least three times. The final pellet was dissolved in toluene and stored inside a nitrogen glove box for future use. The NC concentration and diameter was determined by measuring the absorbance at the first exciton absorption maxima and calculated according to Yu, W. W.; Qu, L.; Guo, W.; Peng, X. Chemistry of Materials 2003, 15, 2854. The photoluminescence quantum yield of the 2.6 nm diameter particles was measured to be 0.10 using Rhodamine6G (quantum yield=0.95) as the standard.

Example 8: Optical Experiments

Upconversion Optical Set Up

Upconversion fluorescence spectra were recorded at a right angle to the excitation with an Ocean Optics Inc. JAZ spectrometer. 532 nm laser was obtained from a Coherent Sapphire laser, with an output power of 10.0 mW. The power density is 12.7 W/cm$^2$. A 500 mm focal length lens was used to focus the laser onto the cuvette. The laser source is focused within 1 mm from the front side of the cuvette. This front corner excitation scheme limits the path length of the excitation and emitted light to 1 mm or less inside the cuvette, which minimizes the attenuation of the excitation light and reabsorption of the upconverted light. A lens with focal length of 30 mm was used to couple the signal from upconversion sample into the Ocean Optics Inc. fiber optics. The distance from the sample to the lens, and the lens to the optical fiber are both 60 mm (twice the focal length of the lens). A 532 nm notch filter (Semrock) is used to block the scattered laser light and was inserted right before the optical fiber. The upconversion quantum yield was calculated using Rhodamine 6G as a reference with quantum yield of 0.95 in ethanol.

Absolute Upconversion Quantum Yield Calculation

The upconversion quantum yield (Φuc) is defined by equation S1 as outlined previously in Huang, Z.; Li, X.; Mahboub, M.; Hanson, K. M.; Nichols, V. M.; Le, H.; Tang, M. L.; Bardeen, C. J. Nano Letters 2015, 15, 5552.

$$\Phi_{UC} = 2 \times \Phi_{R6G} \times \frac{n_{DPA}^2}{n_{R6G}^2} \times \frac{[Area]_{DPA}}{[Area]_{R6G}} \times \frac{1 - 10^{-A_{R6G}}}{1 - 10^{-A_{CdSe}}} \quad (S3)$$

where $\Phi_{RG6}$ is the quantum yield of R6G, $n_{DPA}$ and $n_{RG6}$ represent the refractive indices of the solvents for the DPA upconversion sample and R6G, which are hexane and ethanol, respectively. $[Area]_{DPA}$ and $[Area]_{RG6}$ are the integrated areas of the fluorescence peaks of DPA and R6G. $A_{CdSe}$ and $A_{RG6}$ stand for the absorbance of CdSe NCs and R6G at 532 nm.

Figure 9:
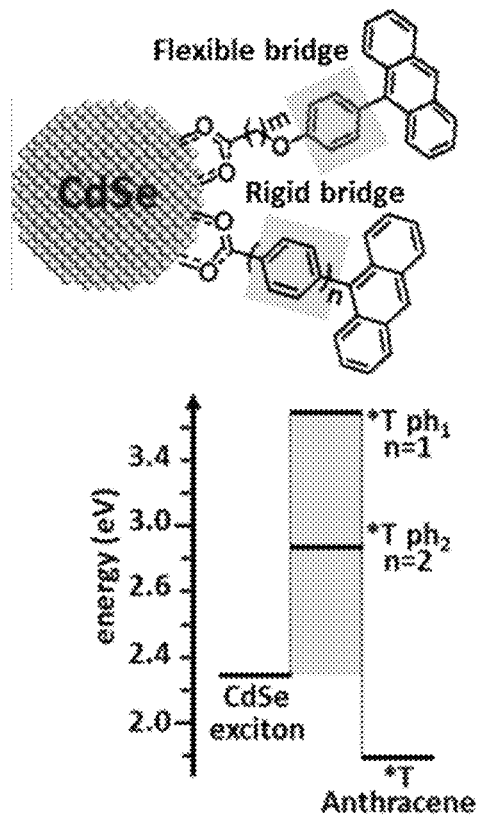
FIG. 9 shows oligo-p-phenylene ($ph_n$) bridged CdSe nanocrystal transmitter ligand complex for investigation of triplet energy transfer is shown. The energy diagram depicts the triplet excitonic states of the CdSe NC, the $ph_n$ bridge when n=1 and 2, and the anthracene transmitter.

As shown in FIG. 9, a series of transmitter ligands described herein are linked to 2.6 nm CdSe NCs through variable-length oligo-p-phenylene or aliphatic bridges with a carboxylic acid group. 2.6 nm diameter CdSe NCs were selected so that the NC band gap is large enough to provide sufficient driving force for energy transfer while allowing for excitation by a 532 nm laser. The energy diagram in FIG. 9 illustrates that the triplet energy transfer from NCs to anthracene is exergonic by roughly 0.55 eV. As emitter molecule, we choose diphenylanthracene (DPA), which is commonly used in organic-organic upconversion schemes due to its long-lived, low-lying triplet state and relatively high (90%) fluorescence quantum yields.

Figure 10:
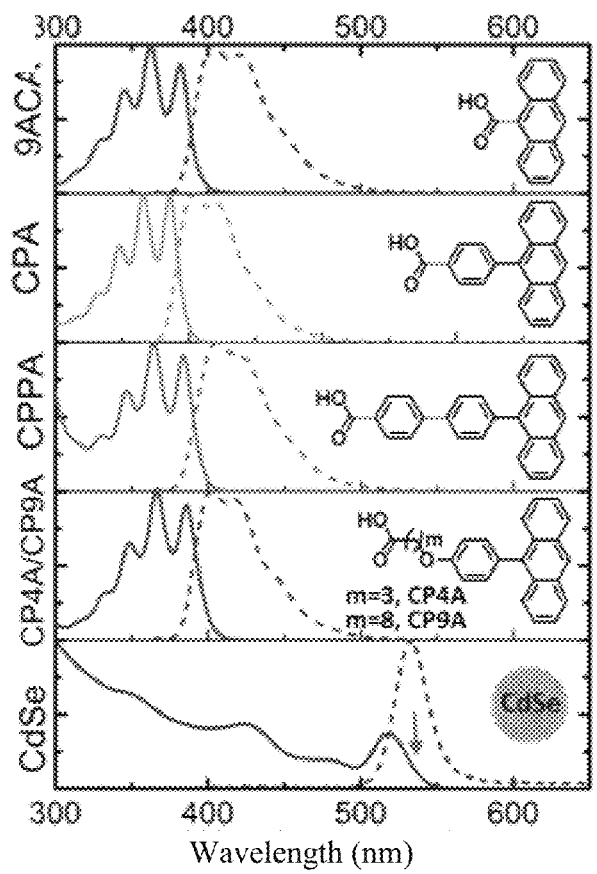
FIG. 10 shows the absorption, fluorescence and photoluminescence spectra for 9ACA, CPA, CPPA, CP4A, CP9A ligands and 2.6 nm CdSe NCs. The spectra were taken at room temperature in hexane, the same solvent as the upconversion experiments. The arrow indicates the 532 nm excitation wavelength for photon upconversion experiments.

The absorption and emission spectra along with the corresponding ligand structures are shown in FIG. 10.

The maximal upconversion QY was found by varying the concentration of anthracene ligands in the ligand exchange solution. The concentration of anthracene ligands in the ligand exchange solution was varied from 13.2 mM to 110.9 mM, while the concentration of CdSe was fixed at 104.6 ∝M (see SI). As carboxylic acid ligands cannot efficiently displace the original phosphonic acid ligands, the ligand exchange reaction was stirred vigorously until the upconversion signal did not improve, which is about 12 h in our case. After stirring, the solution was precipitated with acetone and then redispersed in 2.1 mM DPA solution in hexane for photon upconversion measurements. All upconversion experiments were strictly air free, with samples made inside a glove box and kept in the dark, in airtight fluorescence cuvettes during the entire experimental period. The upconversion QY is defined as follows $$\Phi_{UC} = 2\Phi_{ref} \times \frac{\text{(photons absorbed by reference)}}{\text{(photons absorbed by sample)}} \times \frac{\text{(photons emit by sample)}}{\text{(photons emit by reference)}}$$

Figure 11:
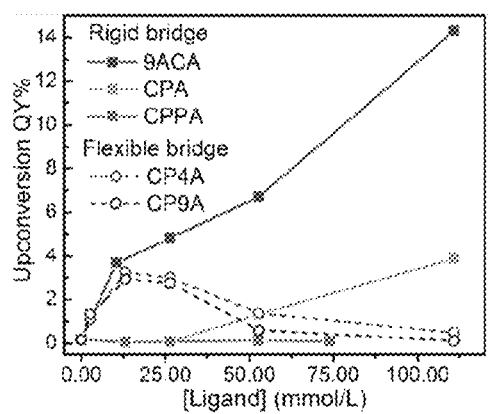
FIG. 11 shows the relationship between upconversion quantum yield versus the concentration of each transmitter ligand during ligand exchange: rigid transmitters (solid square) 9ACA (red), CPA (orange), CPPA (dark yellow); flexible transmitters (hollow circle) CP4A (green) and CP9A (navy). Upconversion samples were prepared in a strictly air free manner and were excited with a 12.7 W/cm² 532 nm laser at RT

The average number of bound anthracene ligands on the surface of one CdSe NC was determined using UV-Vis electronic absorption spectroscopy. The concentration of anthracene ligands and CdSe NCs were obtained using their extinction coefficient at the absorption maxima and first excitonic peak respectively (Table 2). As shown in FIG. 11, the upconversion QY for rigid ligands increases continuously as the concentrations of anthracene transmitter in the ligand exchange solution increases, while it shows a maxima for the flexible ligands. The maximal upconversion QY obtained for 9ACA, CPA and CPPA are 14.3%, 3.9% and 0.4% respectively, and the average values are listed in Table 2. The average values were obtained by measuring the upconversion QY after performing the ligand exchange at these optimized concentrations on at least three separate occasions.

TABLE 2

Adsorption and emission maximum for ligands and CdSe nanocrystals along with extinction coefficients in hexanes at RT.

| | $\lambda_{abs}$ (nm) | $\lambda_{ems}$ (nm) | ε (M⁻¹ · cm⁻¹) × 10⁴ | n | Upconversion QY (%) Average | Upconversion QY (%) Maximum |
|---|---|---|---|---|---|---|
| 9ACA | 362 | 404 | 8.68 | 2.89 | 13.0 | 14.3 |
| CPA | 366 | 405 | 6.85 | 2.34 | 3.5 | 3.9 |
| CPPA | 365 | 405 | 13.8 | 1.72 | 0.30 | 0.40 |
| CP4A | 365 | 403 | 19.1 | 1.28 | 3.0 | 3.3 |
| CP9A | 365 | 403 | 23.3 | 0.78 | 2.6 | 2.9 |
| CdSe | 518 | 534 | 62.6 | N/A | N/A | N/A |

Figure 12:
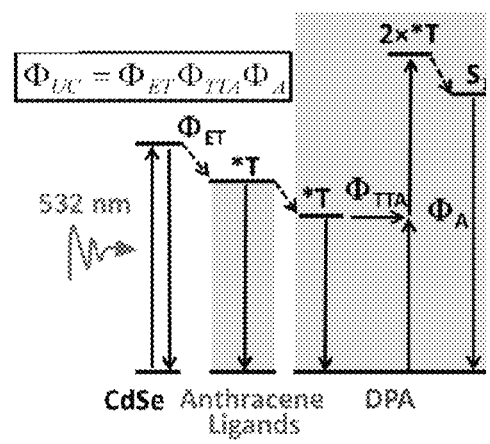
FIG. 12 shows a schematic of the energy transfer in this hybrid photon upconversion platform.

We relate the rate of energy transfer ($k_{et}$) to the efficiency of triplet energy transfer ($\Phi_{ET}$). $\Phi_{ET}$ can be calculated from the measured upconversion QY, $\Phi_{UC}$, based on the following equation, $$\Phi_{UC} = \Phi_{ET}\Phi_{TTA}\Phi_{A} \quad (Eq. 2)$$

where $\Phi_{UC}$, $\Phi_{ET}$, $\Phi_{TTA}$, $\Phi_A$ are the quantum yields of upconversion, energy transfer, triplet-triplet annihilation and acceptor fluorescence respectively (see also FIG. 12). In this work, both $\Phi_{TTA}$ and $\Phi_A$ are constant. $\Phi_A$, the fluorescence QY of DPA is 0.9.[31] As for $\Phi_{TTA}$, standard spin statistics predict that the fraction of triplet-triplet encounters that lead to a singlet is 11.1%. However, the TTA process is usually more efficient since quintet states are not energetically accessible. Here, we use $\Phi_{TTA}$=0.26 based on a report by Monguzzi et. al. for DPA. Based on the maximum upconversion QY measured, $\Phi_{ET}$ is calculated to be 61.1%, 15.8% and 1.7% for 9ACA, CPA and CPPA respectively.

The rate of energy transfer, $k_{et}$, is correlated with the efficiency of energy transfer ($\Phi_{ET}$) by equation 3, which is similar to that previously used by Ding et. al to calculate the yield of hole transfer from CdSe/CdS core/shell NCs to ferrocene $$\Phi_{ET} = \frac{nk_{et}}{k_r + k_{nr} + nk_{et}} \quad (Eq. 3)$$

Figure 13:
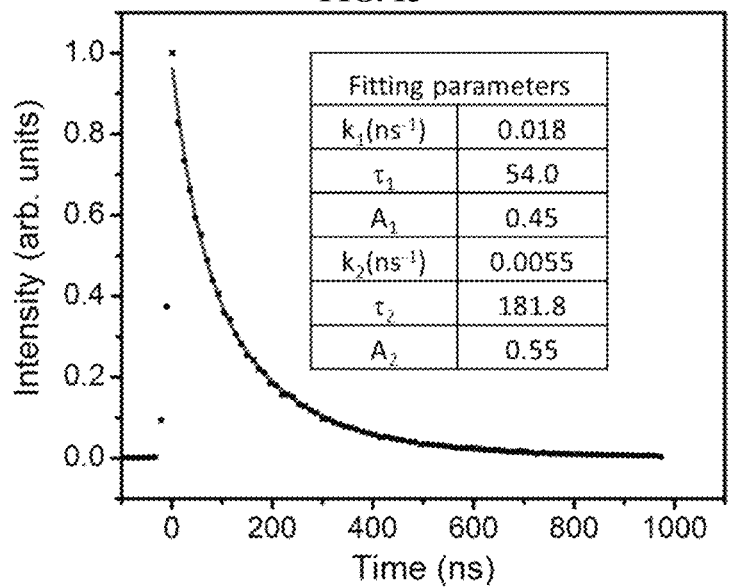
FIG. 13 shows Time resolved photoluminescence measurement of CdSe NCs (black scatter plot). The solid curve shows the experimental data can be fit with a biexponential decay. The fitting parameters, $A_i$, $k_i$ and $\tau_i$, are given in the inset, where i=1 and 2, corresponding to the first and second time constants.

In equation 3, n is the average number of bound anthracene ligands on the surface of NCs, $k_{et}$ is the rate of energy transfer from one CdSe NC to each bound ligand, $k_r$ and $k_{nr}$ are the intrinsic radiative and non-radiative decay rates of CdSe NCs without anthracene ligands. It is assumed that the intrinsic decay rates are unchanged in the presence of the carboxylic acid functionalized ligands, an assumption verified experimentally. The intrinsic decay of CdSe NCs is biexponential with lifetimes of 55 ns and 184 ns respectively (See FIG. 13). Based on time-resolved studies on the kinetics of triplet energy transfer between CdSe and anthracene molecules, energy transfer occurs on the time scale of 70 ns. Therefore, the component with the longer lifetime is more relevant and thus used in equation (3). Detailed fitting parameters and the time-resolved spectrum for CdSe NC can be found in the SI. Here, triplet energy transfer introduces a new decay channel on top of the original intrinsic decay pathways, analogous to the perturbation introduced by charge transfer. However, the average number of bound ligands (n) in our system is small (see Table 2).

Figure 14:
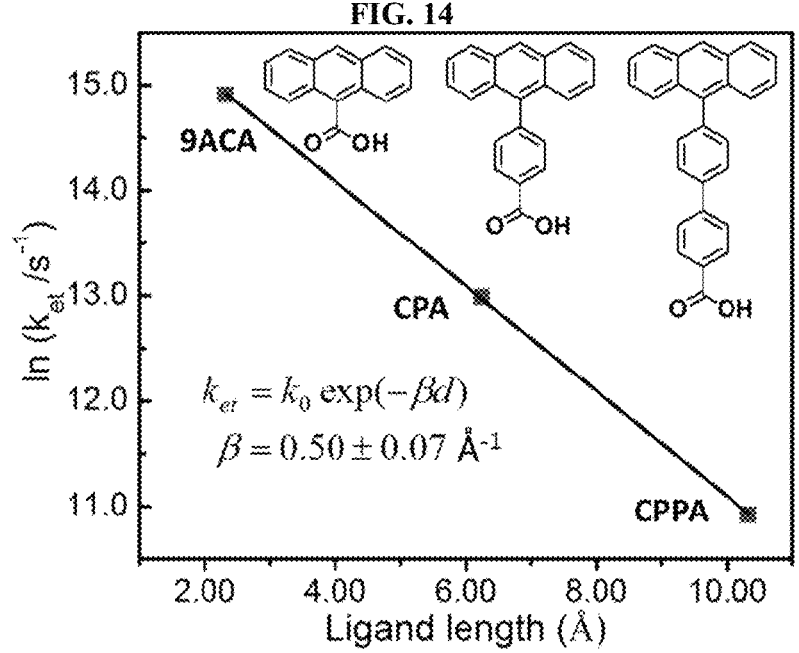
FIG. 14 shows The logarithmic relation of $k_{et}$ versus phenylene bridge length is consistent with Dexter energy transfer. Triplet energy transfer from CdSe NCs to bound anthracene ligands across a phenylene bridge yields a Dexter damping coefficient, β of 0.50±0.07 Å⁻¹.

There is a logarithmic relationship between the donor-acceptor distance and the rate of energy transfer ($k_{et}$), consistent with Dexter energy transfer as the dominant mechanism (FIG. 14). The distance dependence of $k_{et}$ can be described by equation 4, where d is the length of the energy barrier and β is an empirical damping coefficient that describes the extent of coupling through the barrier material.

$$k_{et} = k_0 \exp(-\beta d) \quad \text{(Eq. 4)}$$

Figure 15:
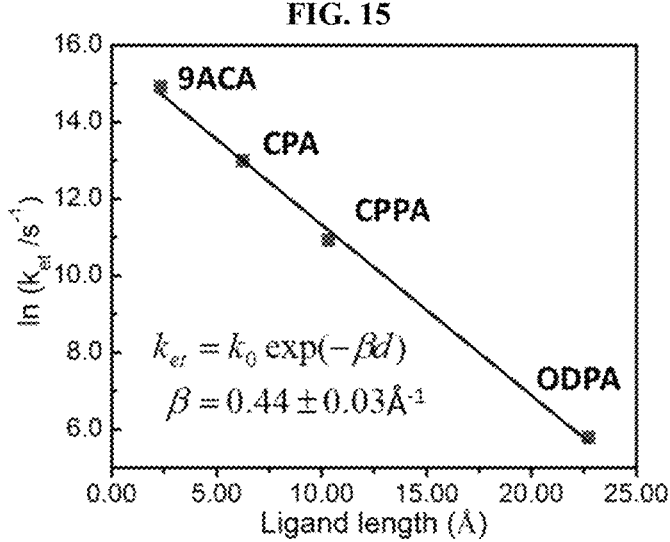
FIG. 15 shows the logarithmic relation of $k_{et}$ versus phenylene bridge length is consistent with Dexter energy transfer. A data point for the original ODPA-capped CdSe NCs is included. The Dexter damping coefficient, β is 0.44±0.03 Å⁻¹. For the ODPA-capped CdSe NCs that did not undergo ligand exchange, n, the average number of DPA molecules involved in energy transfer is estimated considering the surface area of the NC and the concentration of DPA in the upconversion solution. If the radius of ODPA capped CdSe NC is estimated as the sum of the length of the ODPA ligand (2.3 nm) and the radius of CdSe core (1.3 nm), the surface area of a CdSe NC is 159.18 nm². The 9,10-diphenylanthracene molecules is modeled as a 9.22 Å long and 13.23 Å wide rectangle, so the area occupied by each DPA molecule is estimated to be about 1.22 nm², assuming DPA's long axis is parallel to the NC surface. The maximum number of DPA molecules on the surface of 2.6 nm diameter CdSe NC is therefore calculated to be 130. Alternatively, taking into account the concentration of DPA (2.1 mM), the number of DPA molecules in a 4 Å shell about this nanocrystal is 134, again assuming the long axis of the DPA is parallel to NC surface. Note that both these calculations provide a minimum n value, hence the $k_{et}$ value for the ODPA only sample is an upper bound.

The experimentally determined β for the CdSe-(phenylene)$_n$-anthracene system is found to be 0.50±0.07 Å$^{-1}$. If we include the original, unfunctionalized ODPA-capped CdSe NCs, where the upconversion QY is 0.026%, then β is 0.44±0.02 Å$^{-1}$ (see FIG. 15). The same experimental result was reproduced on another batch of 2.6 nm CdSe NCs for a β value of 0.57±0.04 Å$^{-1}$. The value of β depends on the energy offset between the donor and acceptor (0.55 eV here), as well as the height and length of the tunneling barrier between the two species. In the case of the CdSe-(phenyl)-anthracene system, the length of the phenyl bridge is systematically elongated by increasing the number of phenylene units from 0 to 2 going from 9ACA to CPA to CPPA. However, the barrier height is not constant, because the first excited triplet states of benzene and bisphenylene are 3.67 and 2.85 eV respectively, as drawn in FIG. 9. Nonetheless, the β value obtained here is comparable to that measured in organic donor-acceptor systems. In the case of hole transfer from a perylene-3,4:9,10-bis(dicarboximide) donor to a phenothianzine acceptor, the rate constant had a strong distance dependence with a β value of 0.46 Å$^{-1}$. In terms of triplet-triplet energy transfer, a Ru(bpy)$_3^{2+}$(bpy=2,2'-bipyridine)-phenylene bridge-Os(bpy)$_3^{2+}$ system was found to obey Dexter-type transfer, leading a β value of 0.50 Å$^{-1}$. In both cases, the high energy barrier imposed by the oligo-p-phenylene bridge resulted in the tunneling of energy or charge. The tunneling barrier created by the phenylene bridge between the CdSe NC and anthracene impedes efficient energy transfer, leading to a strong distance dependence. In our case, the carboxylic acid group may also contribute to the tunneling barrier. In terms of NC-molecule systems, a value of β=0.24 Å$^{-1}$ and 0.85 Å$^{-1}$ was reported for hole transfer from CdSe NC donors to ferrocene acceptors across CdS and alkyl barriers respectively. A lower β value indicates stronger coupling, or a lower tunneling barrier$_{49}$, and the values measured here compare well considering the dielectric constants and energetic barriers introduced by the spacer.

Another way of quantifying the efficiency of energy transfer, $\Phi_{ET}$, is by relating any change in NC PL to the triplet sensitization of anthracene. As shown in equation (5), $\Phi_{ET}$ can be calculated from the change in steady-state NC PL during the upconversion experiments where $F_{DA}$ and $F_D$ represent the CdSe emission peak intensities in the presence and absence of anthracene ligands respectively. In order to distinguish the $\Phi_{ET}$ calculated using the upconversion QY from equation (2), we relabeled the $\Phi_{ET}$ here as $\Phi_{ET(NC)}$. Here, $F_D$ represents the emission of the CdSe NCs functionalized with a carboxylic acid ligand without a transmitter anthracene unit, e.g. benzoic acid, butyric acid and octanoic acid. The introduction of these carboxylic acid ligands does not appreciably change the NC PL, unlike amine or thiol based ligands.

$$\Phi_{ET(NC)} = 1 - \frac{F_{DA}}{F_D} \quad \text{(Eq. 5)}$$

Figure 16:
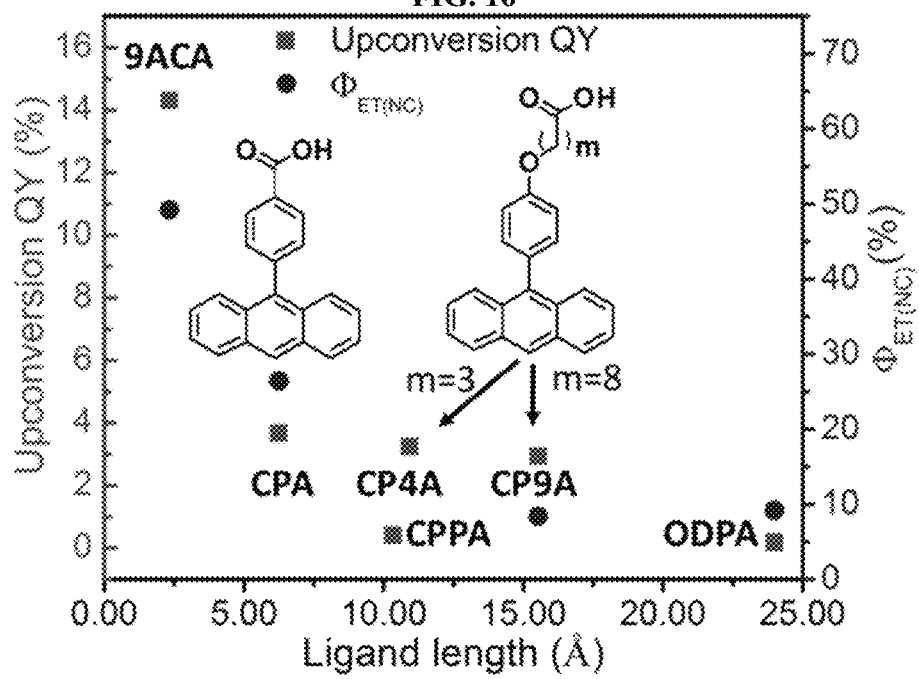
FIG. 16 shows a plot of the optimal upconversion quantum yield (QY) for each anthracene transmitter, There is a strong distance dependence in the family of rigid ligands (9ACA, CPA and CPPA), while for the flexible ligands, CP4A and CP9A, the upconversion QYs are similar to each other and to CPA. $\Phi_{ET}$(NC) determined from equation (5) follows the same trend as this maximum upconversion QY for each transmitter.

FIG. 16 shows $\Phi_{ET(NC)}$ determined via equation (5) has the same trend as the upconversion QY, but only to a limited extent. For example, though the CPPA and ODPA ligands result in the same upconversion QY, in the presence of 2.1 mM DPA, the CdSe PL is not affected by the former while it is quenched by 10% for the latter. The low average number of bound ligands and the strong distance dependence leads to a weak effect on NC PL for ligands with a long bridge. Therefore, we cannot assign a $\Phi_{ET(NC)}$ value based on equation (5) for CPPA and CP4A since these ligands do not quench the NC. Indeed, even for 9ACA, the transmitter which gives the highest upconversion QY of 14.3%, ΦET (NC)=50%, indicating that the NC PL is only half quenched by triplet energy transfer. Work is underway in this laboratory to design ligands with a lower energy barrier and better chemical affinity for the NC surface.

The flexible aliphatic transmitter ligands, CP4A and CP9A, give an unexpectedly high upconversion QY that shows no distance dependence. For both transmitters, the upconversion QY peaks at a ligand exchange concentration of 13.2 mM for a value of about 3.0%. Though this is similar to the optimized upconversion QY of the rigid CPA ligand, Table 1 shows that the average number of transmitters per NC, n, is lower for CP4A (n=0.78) and CP9A (n=1.28) compared to CPA (n=2.34). Given the fact that the fully extended spacer lengths for CPA, CP4A and CP9A are drastically different (6.2 Å, 10.9 Å and 15.5 Å respectively), the consistency in upconversion QY is quite surprising. Note that the unifying motif between these three transmitters is the single rigid phenyl group separating the anthracene moiety from the NC surface. A similar trend was also observed when we performed the same experiment on a different batch of 2.6 nm CdSe NCs (see FIG. 13). Therefore we infer that the lack of distance dependence in the upconversion QY for the aliphatic ligands as strong evidence that these flexible molecules bend over on the surface of CdSe NC, either through thermal fluctuations or a curved ligand binding geometry. Interestingly, as the concentration of CP4A and CP9A in the ligand exchange solution increases from 13.2 mM to the maximal 110.9 mM, the up conversion QY drops dramatically to about 0.11%. Though we did not observe any clear shifts in the absorption spectra of the hybrid complex, we cannot rule out the possibility that excimer formation may reduce $\Phi_{UC}$ under higher ligand loading. It is possible that transmitter ligands with flexible alkyl chains may bind to different sites on the NC, insert and interact with the native octadecylphosphonic acid (ODPA) ligand network differently compared to the rigid 9ACA, CPA and CPPA molecules.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

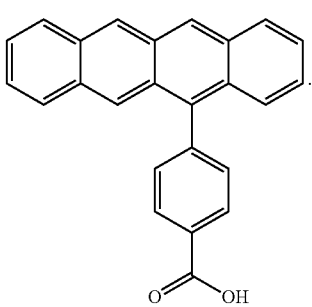 [SMILES: O=C(O)c1ccc(-c2c3ccccc3cc3cc4ccccc4cc23)cc1]

16. The photon upconversion hybrid system of claim 8, wherein said nanocrystal transmitter ligand comprises a PbS nanocrystal and a transmitter ligand having the Formula
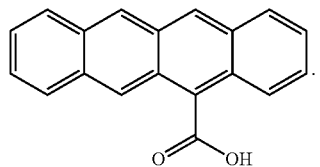 [SMILES: O=C(O)c1c2ccccc2cc2cc3ccccc3cc12]

What is claimed is:

1. A nanocrystal transmitter ligand complex for photon upconversion comprising a lead semiconductor nanocrystal and a transmitter ligand of Formula II

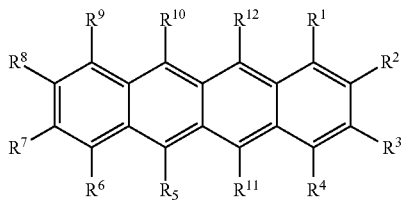

(II)

wherein, $R^1$, $R^2$, $R^3$, $R^4$, $R^5$, $R^6$, $R^7$, $R^8$, $R^9$, $R^{10}$, $R^{11}$, and $R^{12}$ are independently selected from the group consisting of H, —$X^1$—C(O)OH, —$X^1$—C(S)SH, —$X^1$—C(O)SH, —$X^1$—C(S)OH, —$X^1$—NH—C(O)OH, —$X^1$—P(O)(OH)$_2$, —$X^1$—P(O)(OH)$_2$, silyl, and silyloxy;

wherein at least 1 but not more than 4 of $R^1$ to $R^{12}$ are not H;

each $X^1$ is selected from the group consisting of a bond, phenylene, bi-phenylene, $C_1$-$C_{10}$ alkylene, $C_2$-$C_{10}$ alkenylene, $C_2$-$C_{10}$ alkynylene, $C_1$-$C_{10}$ alkylene-phenylene, phenylene-$C_1$-$C_{10}$ alkylene, $C_2$-$C_{10}$ alkenylene-phenylene, phenylene-$C_2$-$C_{10}$ alkenylene, $C_2$-$C_{10}$ alkynylene-phenylene, phenylene-$C_2$-$C_{10}$ alkynylene, $C_1$-$C_{10}$ alkylene-bi-phenylene, bi-phenylene-$C_1$-$C_{10}$ alkylene, $C_2$-$C_{10}$ alkenylene-bi-phenylene, bi-phenylene-$C_{2\text{-}10}$ alkenylene, $C_2$-$C_{10}$ alkynylene-bi-phenylene, bi-phenylene-$C_2$-$C_{10}$ alkynylene.

2. The nanocrystal transmitter ligand complex of claim 1, wherein the lead semiconductor nanocrystal is selected from the group consisting of PbS, PbSe, PbTe.

3. The nanocrystal transmitter ligand complex of claim 1, wherein $R^1$, $R^2$, $R^3$, $R^4$, $R^5$, $R^6$, $R^7$, $R^8$, $R^9$, $R^{10}$, $R^{11}$, and $R^{12}$ are independently selected from the group consisting of H, —$X^1$—C(O)OH, —$X^1$—C(S)SH, —$X^1$—C(O)SH, —$X^1$—C(S)OH.

4. The nanocrystal transmitter ligand complex of claim 1, wherein each $X^1$ is selected from the group consisting of a bond, phenylene, bi-phenylene, $C_2$-$C_{10}$ alkynylene, $C_{1\text{-}10}$ alkylene-phenylene, phenylene-$C_{1\text{-}10}$ alkylene, $C_2$-$C_{10}$ alkynylene-phenylene, and phenylene-$C_2$-$C_{10}$ alkynylene.

5. The nanocrystal transmitter ligand complex of claim 1, wherein the transmitter ligand is represented by Formula IIa,

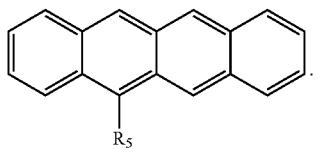

(IIa)

6. The nanocrystal transmitter ligand complex of claim 1, wherein the transmitter ligand is represented by Formula IIb,

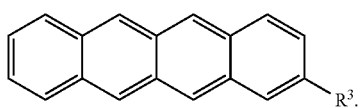

(IIb)

7. The nanocrystal transmitter ligand complex of claim 1, wherein the transmitter ligand is represented by Formula IIc

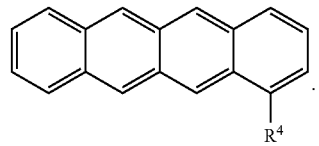

(IIc)

8. A photon upconversion hybrid system comprising a nanocrystal transmitter ligand complex of claim 1 and an annihilator.

9. The photon upconversion hybrid system of claim 8, wherein said annihilator is selected from the group consisting of 9,10-diphenylanthracene (DPA), 9-(4-phenylethynyl)-10-phenylanthracene, 9,10-bis(phenylethynyl)anthracene (BPEA), pyrene, BODIPY dye molecules, and rubrene.

10. The nanocrystal transmitter ligand complex of claim 1, wherein said transmitter ligand is selected from the group consisting of

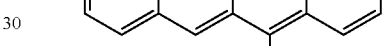

,

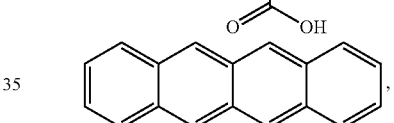

,

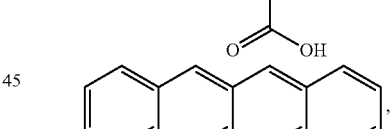

,

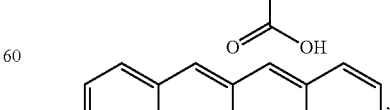

,

-continued

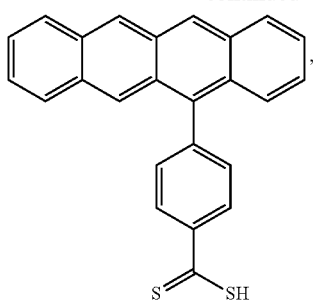 [SMILES: O=C(O)c1ccc(-c2c3ccccc3cc3cc4ccccc4cc23)cc1]

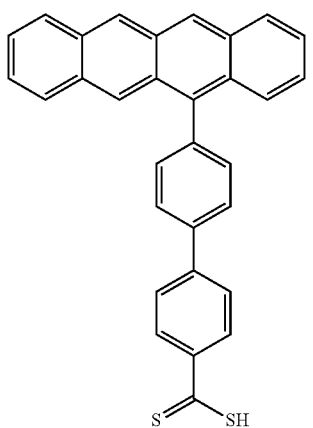

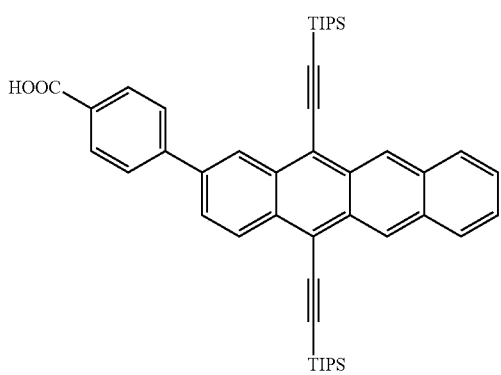

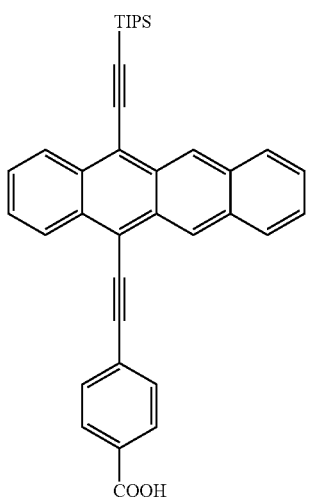

-continued

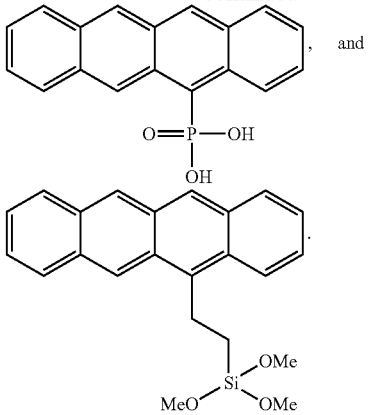

and

11. A method for non-invasive bio-imaging and/or non-invasive bio-detection, said method comprising administering to a subject one or more photon upconversion hybrid systems of claim 8, and bio-imaging or bio-detecting the one or more photon upconversion hybrid systems in the subject.

12. The method of claim 11, wherein said one or more photon upconversion hybrid systems are incorporated into a nanoemulsion.

13. The nanocrystal transmitter ligand complex of claim 1, wherein said transmitter ligand has the Formula

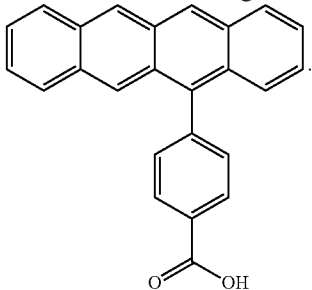

14. The nanocrystal transmitter ligand complex of claim 1, wherein said transmitter ligand has the Formula

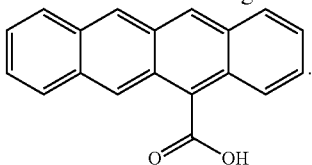

15. The photon upconversion hybrid system of claim 8, wherein said nanocrystal transmitter ligand comprises a PbSe or PbS nanocrystal and a transmitter ligand having the Formula